(12) United States Patent
Goldberg et al.

(10) Patent No.: US 6,882,417 B2
(45) Date of Patent: Apr. 19, 2005

(54) METHOD AND SYSTEM FOR DETECTING DEFECTS

(75) Inventors: Boris Goldberg, Ashdod (IL); Ron Naftali, Shoham (IL)

(73) Assignee: Applied Materials, Inc., Santa Clara, CA (US)

( * ) Notice: Subject to any disclaimer, the term of this patent is extended or adjusted under 35 U.S.C. 154(b) by 283 days.

(21) Appl. No.: 10/105,530

(22) Filed: Mar. 21, 2002

(65) Prior Publication Data

US 2003/0179370 A1 Sep. 25, 2003

(51) Int. Cl.$^7$ .............................................. G01N 21/88
(52) U.S. Cl. ................... 356/237.4; 356/237.5
(58) Field of Search ............... 356/237.1, 237.2–237.5, 356/51, 124, 318, 326, 401, 456; 359/619, 621, 727, 245, 291, 308, 337, 348

(56) References Cited

U.S. PATENT DOCUMENTS

| | | | |
|---|---|---|---|
| 5,177,559 A | * | 1/1993 | Batchelder et al. ...... 356/237.5 |
| 5,699,447 A | | 12/1997 | Alumot et al. ............... 382/145 |
| 5,768,017 A | * | 6/1998 | King et al. .................. 359/559 |
| 6,064,517 A | | 5/2000 | Chuang et al. ............. 359/364 |
| 6,122,046 A | | 9/2000 | Almogy .................... 356/237.2 |
| 6,178,257 B1 | | 1/2001 | Alumot et al. ............... 382/145 |
| 6,259,093 B1 | | 7/2001 | Wakiyama et al. ......... 250/306 |

* cited by examiner

*Primary Examiner*—Richard A. Rosenberger
*Assistant Examiner*—Vincent P. Barth
(74) *Attorney, Agent, or Firm*—Blakely, Sokoloff, Taylor & Zafman

(57) ABSTRACT

System for scanning a surface, including a light source producing an illuminating light beam; an objective lens assembly, located between the light source and the surface; at least one light detector; an apodizator located between the light source and the objective lens assembly; and a relay lens assembly located between the apodizator and the objective lens assembly, wherein the light source produces an image of the illuminating light beam on the apodizator, the apodizator blocks at least a portion of the illuminating light beam, the relay lens assembly images the blocked illuminating light beam at an entrance pupil of the objective lens assembly, and wherein at least one of said at least one light detector, detects light reflected from said surface.

45 Claims, 26 Drawing Sheets

METHOD AND SYSTEM FOR DETECTING DEFECTS

FIELD OF THE DISCLOSED TECHNIQUE

The disclosed technique relates to systems and methods for detecting defects and anomalies in surfaces, in general and to systems and methods for detecting defects and anomalies in silicon wafer used in the production of semiconductor devices, in particular.

BACKGROUND OF THE DISCLOSED TECHNIQUE

A silicon wafer is etched by using different photographic masks to produce large-scale integrated (LSI) semiconductor circuits, very-large-scale integrated (VLSI) semiconductor circuits or ultra-large scale integrated (ULSI) semiconductor circuits. In general, a photographic mask is imprinted with a predetermined pattern. The pattern is then imprinted on the wafer by various lithographic methods. It shall be appreciated by those skilled in the art that the pattern imprinted on the wafer should be essentially identical to the predetermined pattern. Any deviation from the predetermined pattern would constitute a defect and shall render that wafer defective. Also, any imperfection on the non-etched surface of the silicon wafer (such as pits, scratches, foreign matter particles etc.) may also constitute an undesirable defect.

Hence, it is important to detect such defects. When a defect is detected, either at least a portion of the wafer is discarded or the defect is analyzed to determine if it constitutes a critical defect or a nuisance defect (a defect which will not adversely affect performance). Therefore it is important that the inspection system does not declare "false defects" (i.e., declare a defect for a non-defective wafer).

Semiconductor circuits are becoming more and more complex, condensed in structure and smaller in size, and are thus more prone to defects. A conventional method for detecting defects often includes several different test procedures.

Conventional optical inspection system, utilize bright-field, dark-field and gray-field detection based techniques. Bright-field, dark-field and gray-field based techniques, are generally defined as imaging techniques wherein the detected image is completely bright, completely dark, or partially bright, respectively, in the absence of a specimen.

In a simple bright-field based technique, an illumination system illuminates a specimen from above, and a collection optical system located above or below the specimen, detects the light reflected or scattered from the specimen. The broadest definition of bright-field light refers to light thus collected. It is noted, however, that other techniques use different definitions of a bright-field light beam, as shall be described herein below.

In a typical dark-field based technique, either the specimen is illuminated from above and light reflected there from is collected from the sides, or the specimen is illuminated from the side and light reflected there from is collected from above. The light thus collected is typically referred to as the dark-field light beam. A typical gray-field based technique shall be discussed herein below with reference to FIG. 1.

U.S. Pat. No. 6,178,257 entitled "Substrate Inspection Method and Apparatus", U.S. Pat. No. 5,699,447 entitled "Two-Phase Optical Inspection Method and Apparatus for Defect Detection", and U.S. Pat. No. 5,982,921 entitled "Optical inspection method and apparatus", all issued to Alumot et al. and assigned to the assignee of the present disclosed technique, describe a dark-field detection system, and are incorporated herein by reference. U.S. Pat. No. 6,122,046 issued to Almogy et al., entitled "Dual Resolution Combined Laser Spot Scanning and Area Imaging Inspection", and assigned to the assignee of the present disclosed technique, describes a detection system utilizing a technique combining dark-field and bright-field imaging, and is also incorporated herein by reference.

U.S. Pat. No. 6,259,093 issued to Wakiyama et al., entitled "Surface Analyzing Apparatus", is directed to an apparatus for the detection of foreign matter and defects on a wafer surface. A polarized laser light is scattered from the wafer surface and is detected in an optical microscope. Since the pattern imprinted on the wafer causes a constant polarization in the reflected light, an appropriate polarizing mask on the microscope side, reduces the intensity of the reflected light. However, the light reflected from surface defects and foreign matter is significantly less influenced by the mask and hence does not exhibit a reduction in brightness, and is therefore detectable (i.e., distinguished from the polarized light).

U.S. Pat. No. 5,699,447 issued to Alumot et al., entitled "Two-phase optical inspection method and apparatus for defect detection", is directed to a method for detecting defects on patterned wafers. The wafer is illuminated and light diffracted from the wafer surface is collected by a plurality of detectors, arranged in a circular pattern around the inspected wafer.

U.S. Pat. No. 6,064,517 issued to Chuang et al., entitled "High NA System for Multiple Mode Imaging", is directed to an inspection apparatus which provides different imaging modes, such as dark-field and bright-field. The apparatus includes a high numerical aperture catadioptric (using both reflection and refraction to form an image) optical group which forms an intermediate image, the image is then corrected for aberrations by a focusing group and mapped to a plane located at a pupil of the system. Apertures placed at this plane can be used to limit the range of scattering angles reaching the image detector.

U.S. Pat. No. 6,122,046 issued to Almogy et al., entitled "Dual Resolution Combined Laser Spot Scanning and Area Imaging Inspection", is directed to an apparatus for optically detecting defects in a silicon substrate. A linearly polarized light beam is passed through a beam splitter, which is aligned so as to transmit the illuminating light beam without deflection. The illuminating light beam then passes through a quarter wave plate which circularly polarizes it. The illuminating light beam is then reflected from the inspected surface. The reflected light passes through the quarter wave plate in the opposite direction and is linearly polarized thereby, but in a direction perpendicular to the original linear polarization direction of the illuminating light beam. The reflected light beam is deflected by the beam splitter, due to its perpendicular polarization, toward a bright-field detector.

The article "Detection of Fibers by Light Diffraction", J. List et al. (1998), describes an apparatus for the detection of asbestos fibers in air flow. The device described detects light scattered from the fibers in the air. A pulsed Nd:YAG laser produces a high intensity illuminating light beam. An apertured mirror is located at the opposite side of the laser source, admitting the illuminating light beam toward a light trap and deflecting light, scattered by the asbestos fibers in the air, toward a light detector (CCD). The apertured mirror protects the light detector from the high intensity illuminating light beam.

Reference is now made to FIG. 1, which is a schematic illustration of a system, generally referenced 10, for scanning a wafer surface, which is known in the art. System 10 is used for scanning a wafer surface 12. System 10 includes a laser light source 14, a scanner 16, a polarizing beam splitter 20, a quarter wave plate 24, an objective lens assembly 26, a relay lens assembly 32, an annular mirror 34, a bright-field detector 36 and a gray-field detector 38.

Laser light source 14, scanner 16, polarizing beam splitter 20, quarter wave plate 24 and objective lens assembly 26 are positioned along a first optical axis 60. Polarizing beam splitter 20, relay lens assembly 32, annular mirror 34 and bright-field detector 36 are positioned along a second optical axis 62. Annular mirror 34 and gray-field detector 38 are positioned along a third optical axis 64.

Polarizing beam splitter 20 includes a semi-transparent reflection plane 22. Reflection plane 22 is oriented at 45 degrees relative to wafer surface 12. Annular mirror 34 is oriented at 45 degrees relative to optical axes 62 and 64. For purposes of simplicity, objective lens assembly 26 is depicted in 2A as a basic objective lens assembly, including an aperture stop 28, located at a pupil of the scanning system, and an objective lens 18. Objective lens 18 has a focal length $F_1$. Aperture stop 28 has a diameter $D_P$.

Laser light source 14 emits a laser light beam 40, which is then received by scanner 16. Scanner 16 expands and redirects laser light beam 40, thereby emitting alternating illuminating light beams at dynamically changing angles and a constant diameter D. The example illustrated in FIG. 1 shows only an illuminating light beam 44, having a maximal scanning angle θ, relative to optical axis 60. Other illuminating light beams (not shown) have scanning angles between θ and −θ.

Illuminating light beam 44 passes through polarizing beam splitter 20 and from there, further through quarter wave plate 24. Quarter wave plate 24 circularly polarizes illuminating light beam 44 in a first angular direction. Illuminating light beam 44 enters objective lens assembly 26 and passes through aperture stop 28. Objective lens assembly 26 focuses illuminating light beam 44 onto a point $30_1$ on wafer surface 12.

Illuminating light beam 44 is reflected and scattered from point $30_1$, in a plurality of directions. Some of the reflected and scattered light is collected by the objective lens assembly, and used to detect the properties of wafer surface 12. According to this technique, the collected light includes a bright-field light beam portion and a gray-field light beam portion. The bright-field light beam is defined as light the portion of collected light which follows the exact path of the illuminating light beam. The gray-field light beam is defined as the rest of the collected light, which is not included in the bright-field light beam. A bright-field light beam 50 and a gray-field light beam 52, of the light scattered and reflected from point $30_1$, are collected by objective lens 18. Objective lens 18 collimates bright-field light beam 50 and gray-field light beam 52, and directs the light beams through aperture stop 28.

Light beams 50 and 52 exit from objective lens assembly 26 circularly polarized in the opposite angular direction as illuminating light beam 44. Light beams 50 and 52 pass through quarter wave plate 24, and become linearly polarized, perpendicular to the polarization of illuminating light beam 44. Light beams 50 and 52 are then reflected off semi-transparent reflection plane 22, and directed to relay lens assembly 32.

Relay lens assembly 32 produces an inverted image of the pupil of aperture stop 28, at the pupil of annular mirror 34. Bright-field light beam 50 passes through the aperture of annular mirror 34. Bright-field detector 36 receives bright-field light beam 50 and detects the intensity thereof. Gray-field light beam 52 is reflected off annular mirror 34. Gray-field detector 38 receives gray-field light beam 52 and detects the intensity thereof.

It is noted that the light beams emitted at other times and having other scanning angles, reach other points on wafer surface 12, between point $30_1$ and another point $30_2$, which is located on the opposite side of optical axis 60 from point $30_1$.

System 10 further includes additional objective lens assemblies (not shown), which are interchangeable with objective lens assembly 26. These objective lens assemblies are mounted on a turret, a slide (both not shown), and the like, which enables interchanging objectives. Each of the different objective lens assemblies is used for a different mode of operation.

Reference is further made to FIGS. 2A and 2B. FIG. 2A is a schematic illustration of objective lens assembly 26 and scanned wafer surface 12 of system 10 (FIG. 1). FIG. 2B is a schematic illustration of an additional objective lens assembly 102 which replaces objective lens assembly 26 (FIG. 2A), and scanned wafer surface 12.

With reference to FIG. 2B, objective lens assembly 102 replaces objective lens assembly 26 (FIG. 2A). It is noted that the optical elements of objective lens assembly 102 are not shown. Objective lens assembly 102 has a focal length $F_2$ equal to $½F_1$, wherein $F_1$ is the focal length of objective lens assembly 26 (FIG. 2A).

Objective lens assembly 102 receives an illuminating light beam $110_1$ of diameter D, and focuses it onto a point $120_1$ on wafer surface 12. Illuminating light beam $110_1$ is similar to illuminating light beam 44 (FIG. 2A), having a maximal scanning angle θ.

Objective lens assembly 102 collects a bright-field light beam $110_1$ having diameter D and a gray-field light-beam $112_1$ having diameter $D_P$. It is noted that objective lens assembly 102 may include various optical elements (e.g., lenses, stops, and the like), which are not shown.

The line between points $30_1$ and $30_2$ (FIG. 2A) on wafer surface 12, is known as the scan line of system 10. It is well known that the scan line length is proportional to the focal length of the objective lens assembly. Hence, the scan line length for the system of FIG. 2B, is approximately ½ of the scan line length of system of FIG. 2A. Furthermore, it is well known that the scanning speed of a scanning system such as system 10 (FIG. 1), is proportional to the square of the scan line length.

It is also well known that the numerical aperture of the scanning light beams of system 10 is inversely proportional to the focal length of the objective lens assembly used. Hence, the numerical aperture for system of FIG. 2B, is approximately 2 times the numerical aperture for system of FIG. 2A. Furthermore, is well known that the scanning resolution for a scanning system such as system 10 is proportional to the numerical aperture.

Thus, by selecting different objectives with different focal lengths, the user of system 10 can choose between a low-speed, high-resolution and a high-speed, low-resolution scan. It is noted that to increase the gray-field numerical aperture, it is required to increase both the numerical aperture of the objective lens assembly and the size of the polarizing beam splitter. The cost of an objective lens assembly and the cost of a polarizing beam splitter, are highly correlated with their respective sizes. Hence, increasing the gray-field numerical aperture for system 10 involves a significant cost increase. It is still further noted that the objective lens assembly is the element of system 10 which is closest to the wafer, located directly there above. Hence, replacing objectives when changing magnification modes, involves a risk of contaminating the inspected wafer.

SUMMARY OF THE DISCLOSED TECHNIQUE

It is an object of the disclosed technique to provide a novel method and system for detecting defects in printed surfaces in general and for detecting defects and anomalies in silicon wafer used in the production of semiconductor devices, which overcomes the disadvantages of the prior art.

In accordance with the disclosed technique, there is thus provided a system for scanning a surface including a light source producing an illuminating light beam, an objective lens assembly, located between the light source and the surface, at least one light detector, an apodizator located between the light source and the objective lens assembly, and a relay lens assembly located between the apodizator and the objective lens assembly. The light source produces an image of the illuminating light beam on the apodizator. The apodizator blocks at least a portion of the illuminating light beam. The relay lens assembly images the blocked illuminating light beam at an entrance pupil of the objective lens assembly. Reflected light collected by the objective lens assembly is directed to at least one of the light detectors, by means of a beam splitter or an annular mirror, or both.

In accordance with another embodiment of the disclosed technique, there is provided a multi-zone gray-field detector, which includes a gray-field collector, a plurality of light detectors and a plurality of light guides. The gray-field collector is divided into a plurality of sections, each defining a detection zone. Each of the light guides optically couples one of the sections with one of the light detectors. Each of the light detector detects at least a portion of light directed thereto, by a respective one of the light guides.

BRIEF DESCRIPTION OF THE DRAWINGS

The disclosed technique will be understood and appreciated more fully from the following detailed description taken in conjunction with the drawings in which:

FIG. 13B is a schematic illustration of the bright-field filter of FIG. 13A and a bright-field light beam incident there upon and partially transmitted there through;

DETAILED DESCRIPTION OF EMBODIMENTS

The disclosed technique overcomes the disadvantages of the prior art by providing a novel method and system for detecting defects in semiconductor manufacturing procedures, using interchangeable telescopes and a single objective.

In the following description the following terms are used:

Illuminating light beam—a light beam originating from a light source and illuminating an inspected object.

Illumination path—the path of the illuminating light beam.

Normally collected light beam—a light beam reflected or scattered off an inspected object and reaching an objective lens above the inspected object.

Collection path—the path of the collected light beam.

Combined path—the intersection of the illumination and collection paths.

Bright-field light beam—the portion of the normally collected light beam coinciding with the illumination path.

Gray-field light beam—the portion of the normally collected light beam not coinciding with the illumination path.

Pupil of a scanning system—a geometric location wherein all the scanning light beams coincide.

The disclosed technique has several aspects. According to one aspect of the disclosed technique, interchangeable telescopes, positioned in the combined path, determine the modes of operation of the scanning system. According to another aspect of the disclosed technique, the combined bright-field and gray-field light beam arrives first at an annular mirror, which separates between the bright-field and the gray-field light beams. According to a further aspect of the disclosed technique, there is provided a novel optical structure for changing the shape of an illuminating light beam, without directly affecting the shape of the respective collected light beams. According to another aspect of the disclosed technique, the apodizators are combined with bright-field filters, which block a selected portion of the bright-field light beam before the bright-field light beam reaches the bright-field detector. According to a further aspect of the disclosed technique, continuous range magnification replaces the discrete values magnification which was provided by the interchangeable telescopes. It is noted that various combinations of the above aspects may be implemented in a single scanning system.

Figure 1:
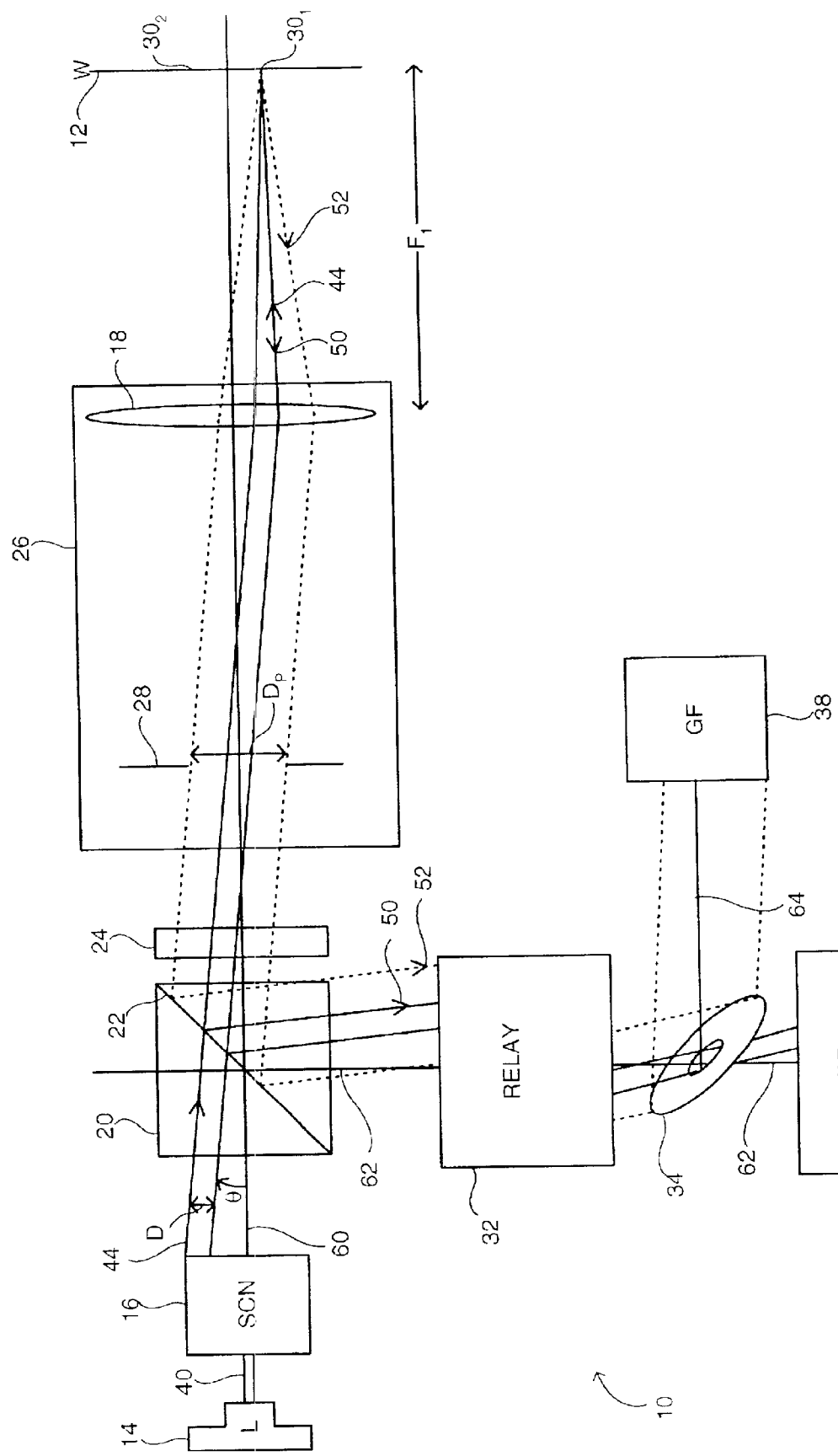
FIG. 1 is a schematic illustration of a system for scanning a wafer surface, which is known in the art.
Figure 2B:
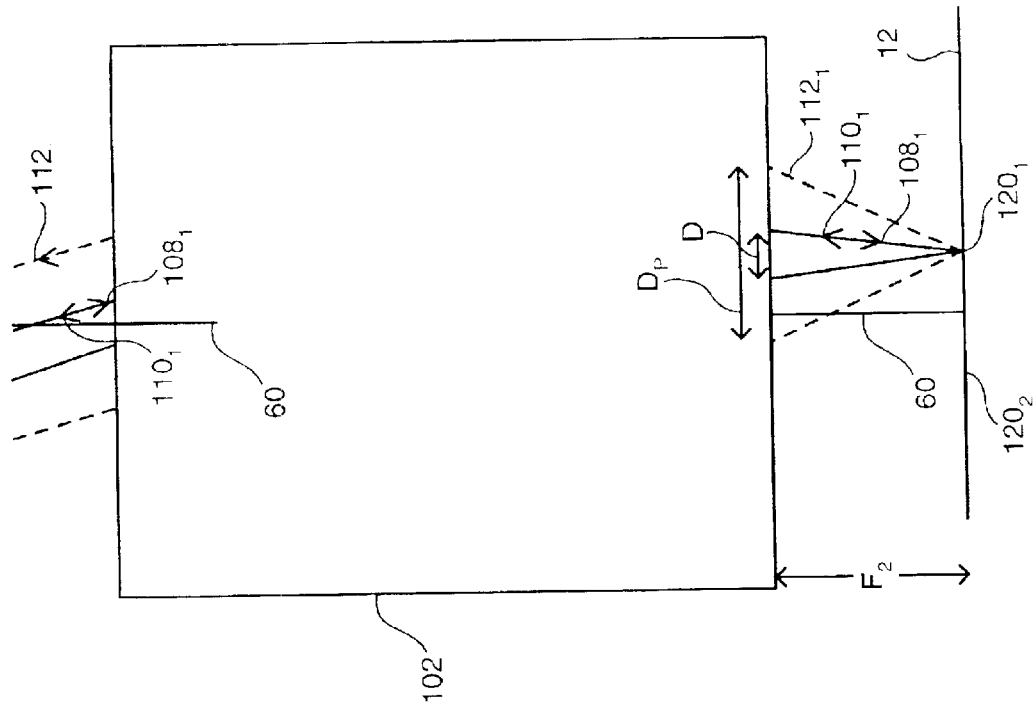
FIG. 2B is a schematic illustration of an additional objective lens assembly which replaces the objective lens assembly of FIG. 2A, and the scanned wafer surface.
Figure 2A:
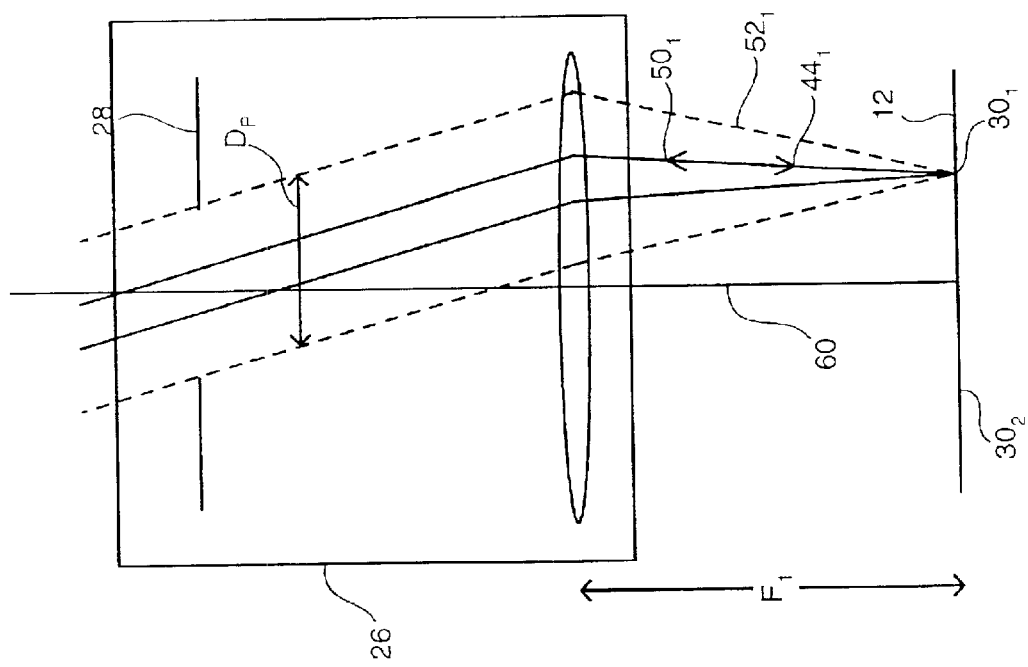
FIG. 2A is a schematic illustration of the objective lens assembly of the system of FIG. 1 and the scanned wafer surface.

According to one embodiment of the disclosed technique, the scanning system illustrated in FIG. 1 is replaced by an alternative scanning system, such as the system illustrated below in FIGS. 3A and 3B. Accordingly, the portion of the scanning system of FIG. 1, which changes according to the selected magnification mode, as illustrated in detail in FIGS. 2A and 2B, is replaced by the portion of the scanning system of FIGS. 3A and 3B, which changes according to the selected magnification mode, as illustrated in detail in FIGS. 4A, 4B and 4C.

Figure 3A:
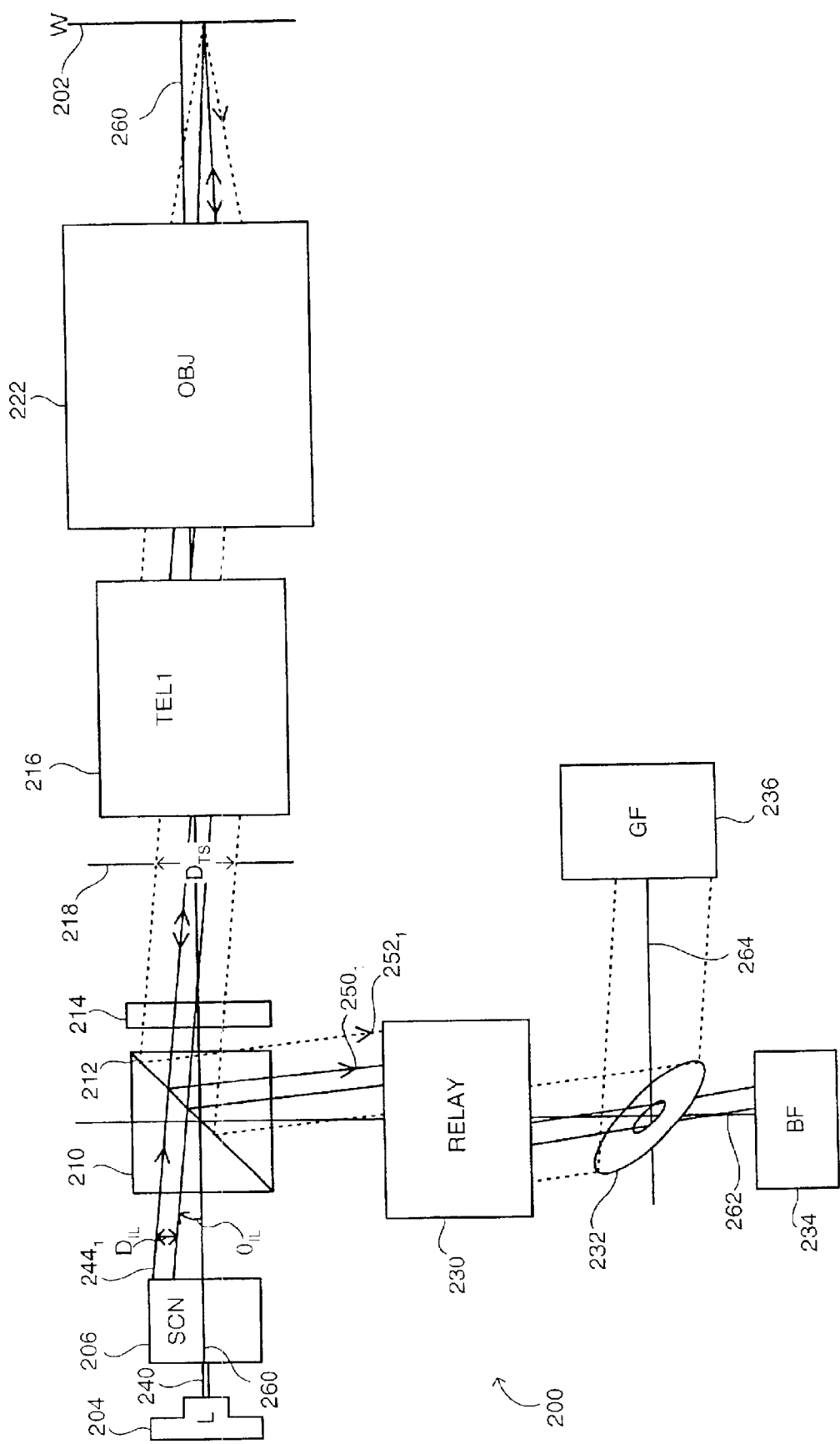
FIG. 3A is a schematic illustration of a system for scanning a wafer surface, constructed and operative in accordance with an embodiment of the disclosed technique, at a first moment in time.
Figure 3B:
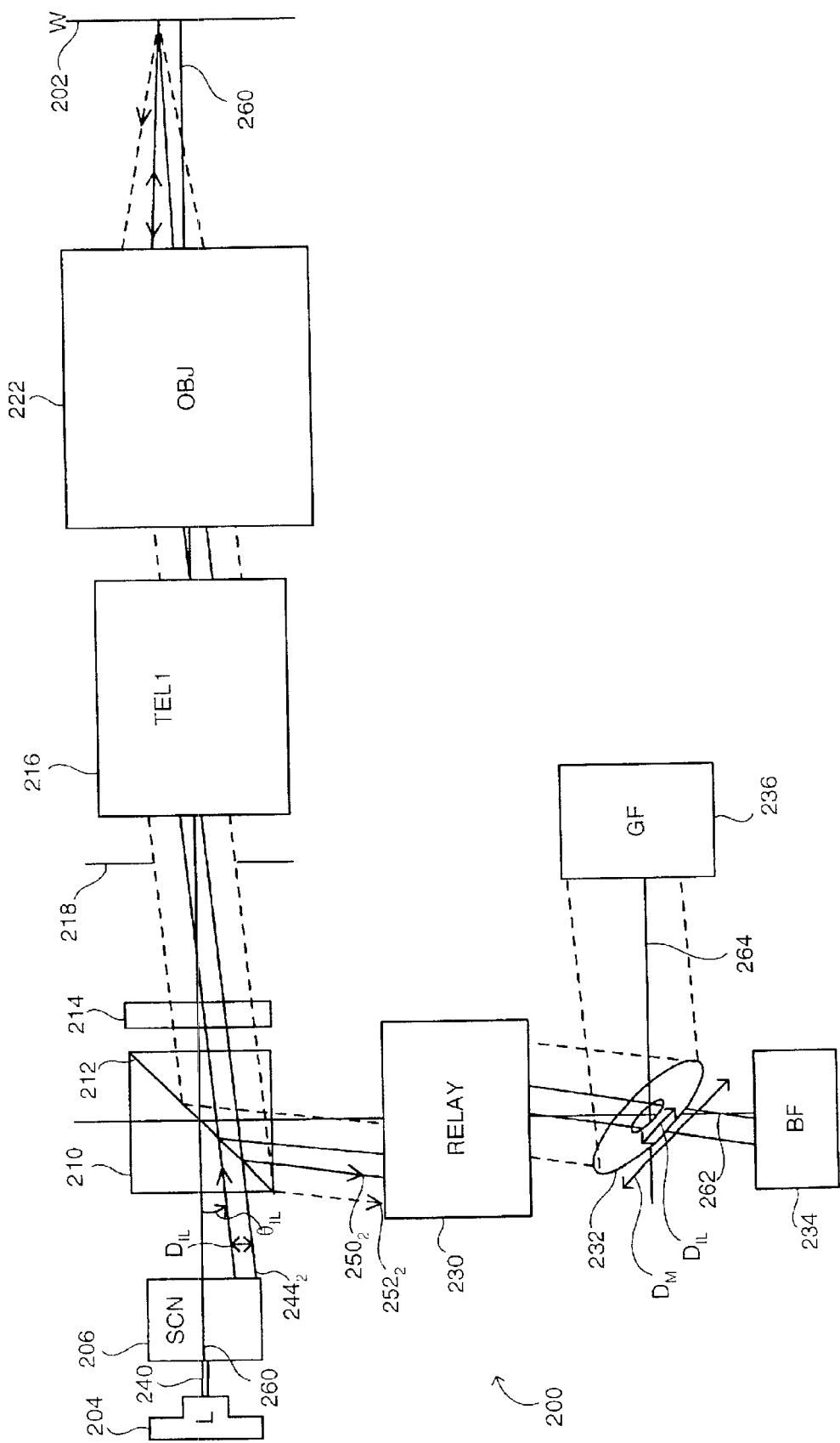
FIG. 3B is a schematic illustration of the system of FIG. 3A, at another moment in time.
Figure 3C:
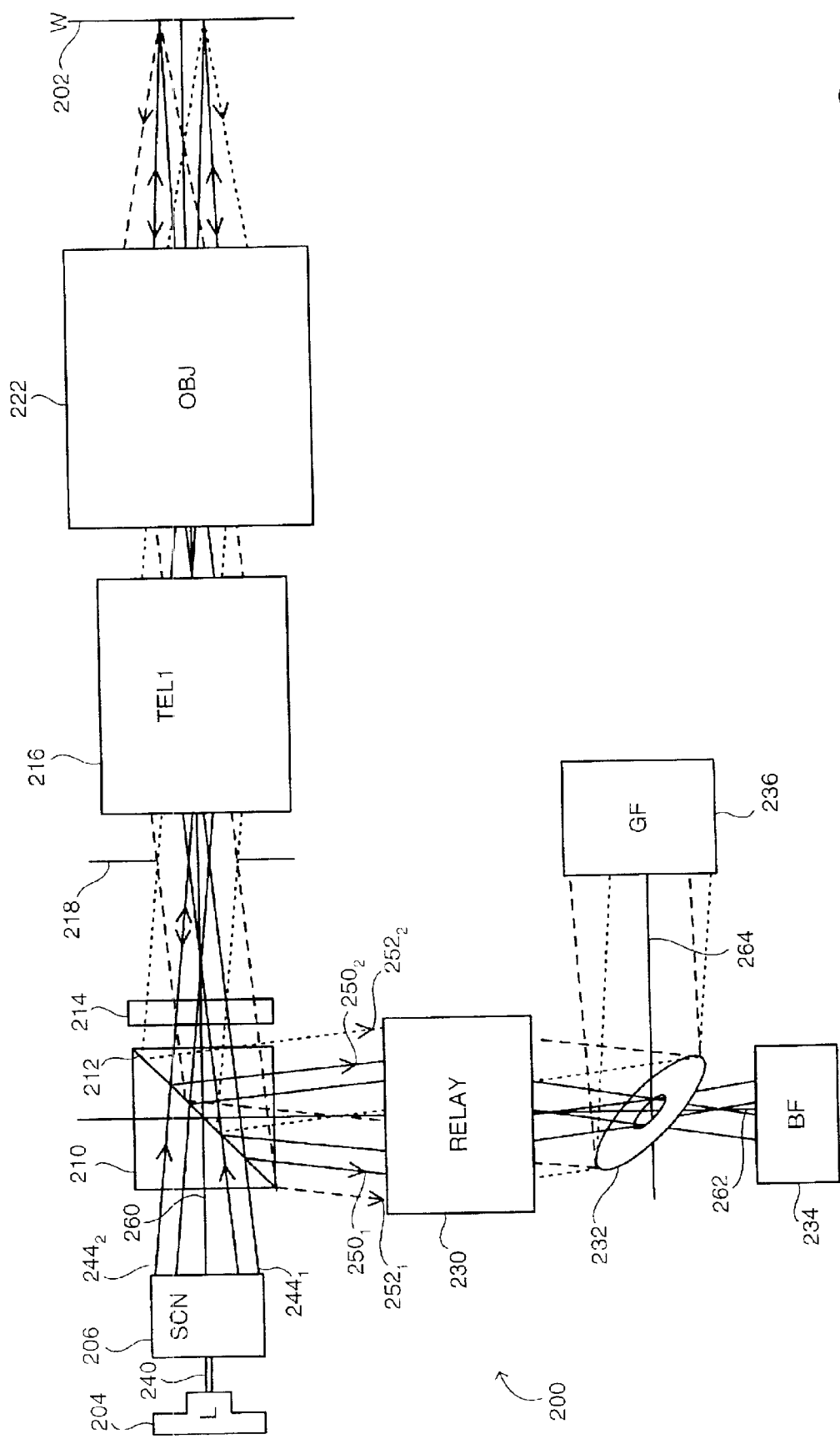
FIG. 3C is a schematic illustration of the system of FIGS. 3A and 3B, including the light beams of both FIGS. 3A and 3B.

Reference is now made to FIGS. 3A, 3B and 3C. FIG. 3A is a schematic illustration of a system, generally referenced 200, for scanning a wafer surface, constructed and operative in accordance with an embodiment of the disclosed technique, at a first moment in time. FIG. 3B is a schematic illustration of the system of FIG. 3A, at another moment in time. FIG. 3C is a schematic illustration of the system of FIGS. 3A and 3B, including the light beams of both FIGS. 3A and 3B.

In the example set forth in FIGS. 3A, 3B and 3C system 200 is used for scanning a wafer surface 202. System 200 includes a laser light source 204, a scanner 206, a polarizing beam splitter 210, a quarter wave plate 214, an aperture stop 218, a telescope 216, an objective lens assembly 222, a relay lens assembly 230, a bright-field detector 234 and a gray-field detector 236.

Laser light source 204, scanner 206, polarizing beam splitter 210, quarter wave plate 214, aperture stop 218, telescope 216, objective lens assembly 222 and wafer surface 202 are positioned along a first optical axis 260. First optical axis 260 is perpendicular to wafer surface 202. Scanner 206 is positioned between laser light source 204 and polarizing beam splitter 210. Quarter wave plate 214 is positioned between polarizing beam splitter 210 and aperture stop 218. Telescope 216 is positioned between aperture stop 216 and objective lens assembly 222. Objective lens assembly 222 is positioned between telescope 216 and wafer surface 202.

Polarizing beam splitter 210, relay lens assembly 230, annular mirror 232 and bright-field detector 234 are positioned along a second optical axis 262. In the present example, second optical axis 262 is perpendicular to first optical axis 260. Relay lens assembly 230 is positioned between polarizing beam splitter 210 and annular mirror 232. Annular mirror 232 is positioned between relay lens assembly 230 and bright-field detector 234.

Annular mirror 232 and gray-field detector 236 are positioned along a third optical axis 264. In the present example, third optical axis 264 is parallel to first optical axis 260.

Polarizing beam splitter 210 includes a semi-transparent reflection plane 212. Semi-transparent reflection plane 212 either transmits or reflects light incident thereupon, depending on the state of polarization of the incident light. In the present example, semi-transparent reflection plane 212 is oriented at 45 degrees relative to wafer surface 202. Quarter-wave plate 214 adds a $\pi/2$ phase (i.e., ¼ of a cycle) to one of the linearly polarized components of light incident there upon. It is noted that quarter-wave plate 214 and polarizing beam splitter 210 may be incorporated in a single module. Annular mirror 232 is located at a pupil of the scanning system. Annular mirror 232 reflects light at all areas thereof (excluding the aperture). In the present example, annular mirror 232 is oriented at 45 degrees relative to optical axes 262 and 264.

It is noted that the annular mirror, which is also known as the apertured mirror, may have various orientations and shapes. For example, the annular mirror may be elliptical, with an elliptical aperture. Accordingly, the inner and outer diameters of annular mirror 232, in the direction perpendicular to the plane defined by optical axes 260 and 262, are $D_{IL}$ and $D_{TP}$, respectively, wherein $D_{TP}$ is the aperture diameter of aperture stop 218, and $D_{IL}$ is the diameter of the illuminating light beams, as explained herein below. Furthermore, the inner and outer diameters of the mirror in the direction of optical axis 264, may be set to at least $\cdot 2 \times D_{IL}$ and $\cdot 2 \times D_{TP}$, respectively, but generally depend also on $\theta_{IL}$, which is the scanning angle, as explained herein below.

Bright-field detector 234 and gray-field detector 236 detect properties of light incident there upon.

Figure 4A:
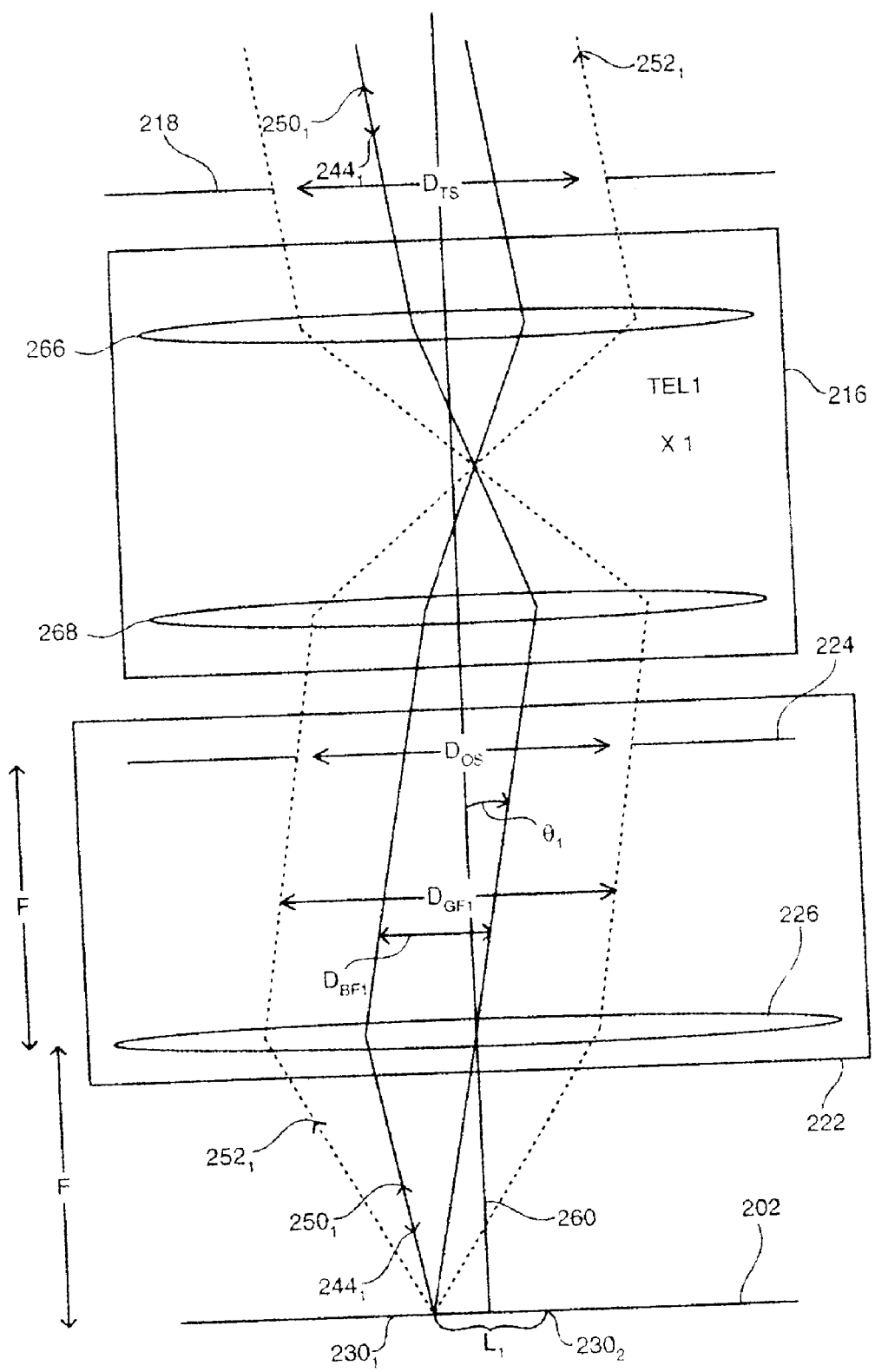
FIG. 4A is an illustration in detail of the aperture stop, telescope and objective lens assembly, of the system of FIG. 3A, at a first moment in time.
Figure 4B:
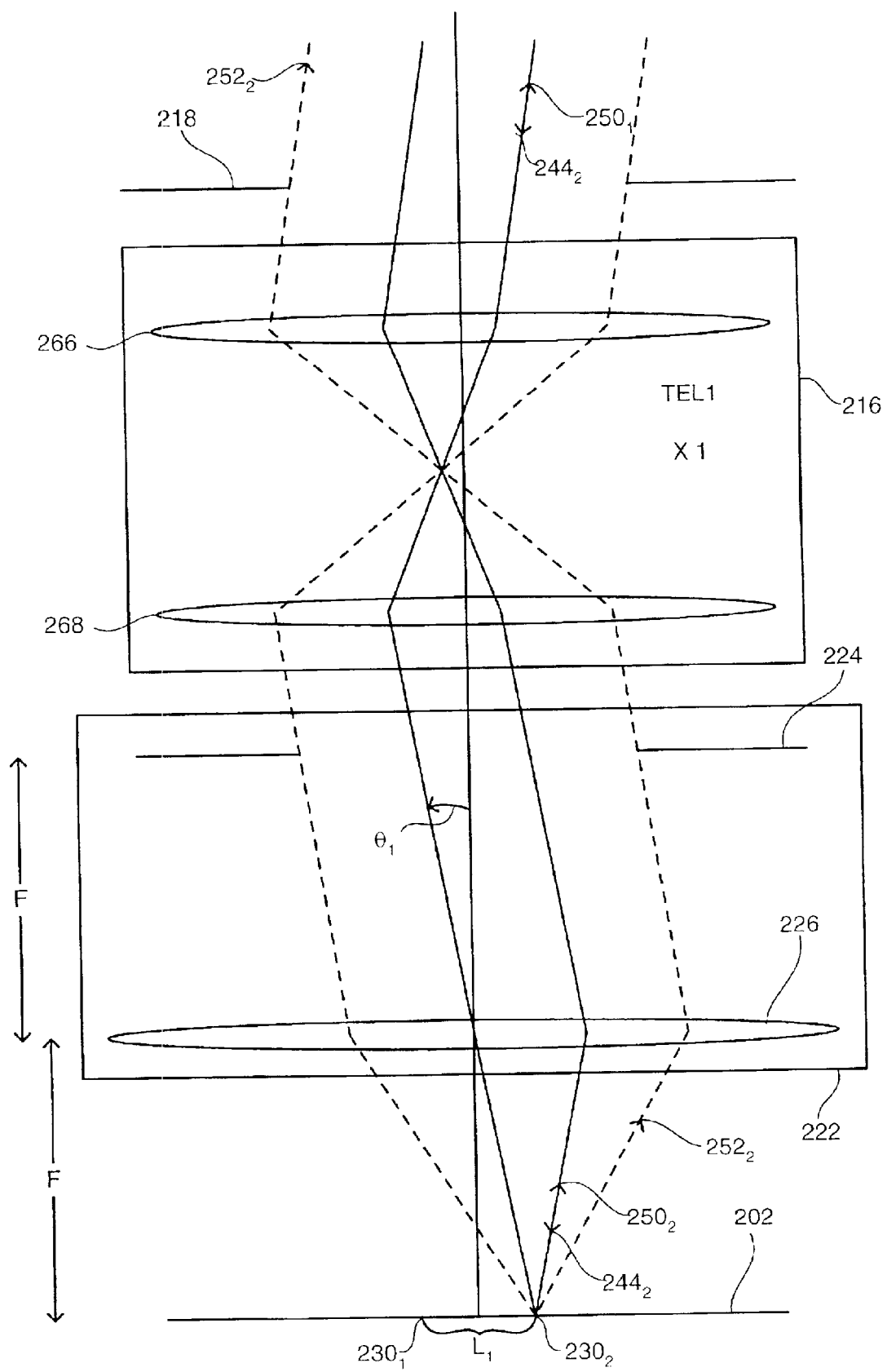
FIG. 4B is an illustration of the elements presented in FIG. 4A, at a second moment in time.
Figure 4C:
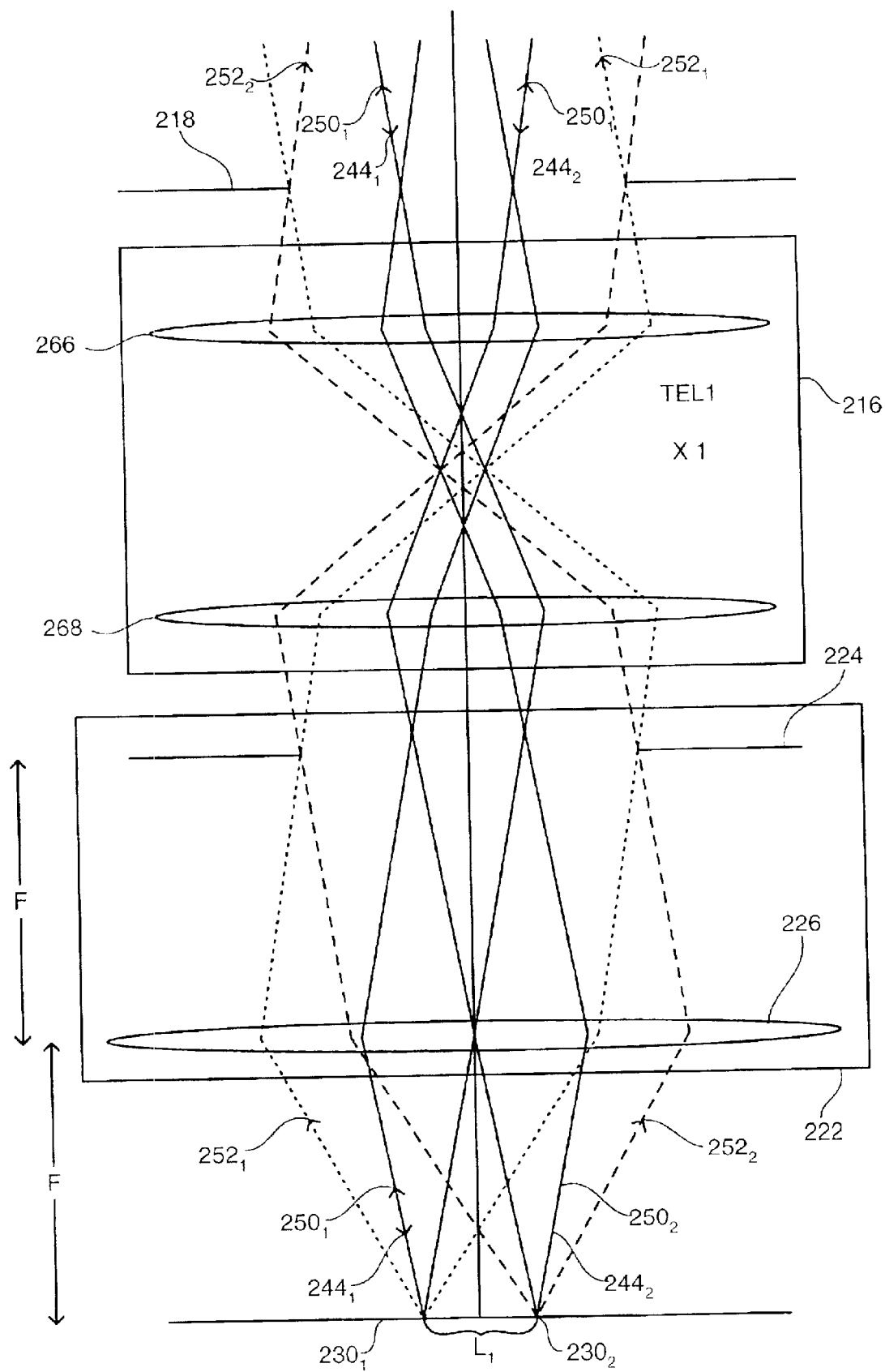
FIG. 4C is an illustration of the elements presented in FIGS. 4A and 4B, including the light beams of both FIGS. 4A and 4B.

Reference is further made to FIGS. 4A, 4B and 4C. FIG. 4A is an illustration in detail of the aperture stop 218, telescope 216 and objective lens assembly 222, of system 200, and scanned wafer surface 202 (FIG. 3A), at a first moment in time. FIG. 4B is an illustration of the system of FIG. 4A, at a second moment in time. FIG. 4C is an illustration of the system of FIGS. 4A and 4B, including the light beams of both FIGS. 4A and 4B.

Aperture stop 218 is located at the entrance pupil of telescope 216. Aperture stop 218 includes an aperture of diameter $D_{TS}$. Aperture stop 218 transmits incident light through the aperture, and rejects (i.e., reflects or absorbs) all other incident light. For example, aperture stop may be an annular non-transmitting disk of inner diameter $D_{TS}$, and a substantially larger outer diameter (e.g., twice as large as the inner diameter).

Telescope 216 includes a first telescope lens 266 and a second telescope lens 268. Telescope lenses 266 and 268 have equal focal lengths. Objective lens assembly 222 includes an objective aperture stop 224 and an objective lens 226. Objective aperture stop 224 is located at the exit pupil of telescope 218, which is also the entrance pupil of objective lens assembly 222. Objective aperture stop 224 has an aperture diameter of $D_{OS}$. In the present example, $D_{TS}=D_{OS}$, wherein $D_{TS}$ is the diameter of aperture stop 218. Objective lens 226 has a focal length F.

For purposes of simplicity, objective lens assembly 222 and telescope 216 are depicted in FIGS. 4A, 4B, and 4C as a basic objective lens assembly and a basic telescope, respectively. It is noted, however, that system 200 may use a more complex objective lens assembly and a more complex telescope instead of objective lens assembly 222 and telescope 216, respectively. Accordingly, the telescope and objective lens assembly may include additional optical elements and may have different dimensions from objective lens assembly 222 and telescope 216, respectively.

Referring back to FIGS. 3A, 3B and 3C, system 200 performs a linear scan of wafer surface 202 by illuminating points on a line on wafer surface 202, collecting the light reflected and scattered there from, and detecting scattered and reflected light. Laser light source 204 emits a laser light beam 240 toward scanner 206. Scanner 206 receives laser light beam 240. Scanner 206 expands and redirects laser light beam 240, thereby producing alternating illuminating light beams $244_1$ and $244_2$, each produced at a different time. Illuminating light beams $244_1$ and $244_2$ are collimated, and linearly polarized in a first predetermined direction of linear polarization. It is noted that for the purpose of simplicity, all of the illuminating light beams mentioned herein, have a circular cross-section, unless otherwise stated.

At a first moment in time, scanner 206 emits illuminating light beam $244_1$, at a diameter $D_{IL}$ and an angle $\theta_{IL}$ relative to first optical axis 260. In the present example, $D_{IL}$ is approximately equal to ¼$D_{TS}$. At a second moment in time, scanner 206 emits illuminating light beam $244_2$, also at diameter $D_{IL}$ and angle $\theta_{IL}$ relative to first optical axis 260. Illuminating light beams $244_1$ and $244_2$ are on opposite sides of first optical axis 260. It is noted that the illumination angle $\theta_{IL}$, is generally small (i.e., $\theta_{IL}<10$ degrees). Hence, small-angle approximations apply.

Illuminating light beam 244, passes through polarizing beam splitter 210 and from there, further through quarter wave plate 214. Quarter wave plate 214 circularly polarizes illuminating light beam $244_1$ in a first angular direction (e.g., clockwise). Illuminating light beam $244_1$ then passes through aperture stop 218 and enters telescope 216.

With reference to FIGS. 4A, 4B and 4C, telescope 216 produces an inverted image of the pupil of aperture stop 218, at the pupil of objective aperture stop 224, at a magnification ratio M=1. Telescope 216 emits light beam $244_1$ at a diameter $D_{BF1}$, and an angle $\theta_1$ relative to first optical axis 260. In general, the angular magnification of a telescope is the reciprocal of the linear magnification of the telescope. The angular magnification and the linear magnification of telescope 216 are both equal to 1. Accordingly, in the present example, $D_{BF1}=D_{IL}$, and $\theta_1=\theta_{IL}$.

Illuminating light beam $244_1$ enters objective lens assembly 222 and passes through objective aperture stop 224. Objective lens assembly 222 focuses illuminating light beam $244_1$ onto a point $230_1$ on wafer surface 202.

Wafer surface 202, depending on the properties of the various elements thereon (e.g., topography, reflectivity, and the like), reflects and scatters illuminating light beam $244_1$ from point $230_1$ in a plurality of directions.

A bright-field light beam $250_1$ and a gray-field light beam $252_1$, of the scattered and reflected light, are received at objective lens assembly 222. Objective lens 226 collimates light beams $250_1$ and $252_1$. Objective lens 226 directs bright-field light beam $250_1$ through objective aperture stop 224 at diameter $D_{BF1}$. Objective lens 226 directs gray-field light beam $252_1$ to objective aperture stop 224 at an outer diameter $D_{GF1}$ and inner diameter $D_{BF1}$. It is noted that the outer diameter $D_{GF1}$ of gray-field light beam $252_1$ may generally depend on both the diameter $D_{OS}$ of objective aperture stop 224 and the diameter $D_{TS}$ of aperture stop 218. In the present example, $D_{GF1}$ is equal to $D_{OS}$ or, equivalently, to $D_{TS}$.

Light beams $250_1$ and $252_1$ pass through objective aperture stop 224 and enter telescope 216. Telescope 216 emits light beams $250_1$ and $252_1$ toward aperture stop 218. Telescope 216 emits bright-field light beam $250_1$ and gray-field light beam $252_1$ towards aperture stop 218, at an outer diameter $D_{TS}$ or, equivalently, $D_{OS}$. Light beams $250_1$ and $252_1$ pass through aperture stop 218. Referring back to FIGS. 3A, 3B and 3C, light beams $250_1$ and $252_1$ then reach quarter wave plate 214. At this stage, light beams $250_1$ and $252_1$ are circularly polarized in the opposite angular direction as light beam $244_1$ (e.g., counterclockwise). Quarter wave plate 214 linearly polarizes light beams $250_1$ and $252_1$ in a direction perpendicular to the linear polarization of illuminating light beam $244_1$. Light beams $250_1$ and $252_1$ then reach polarizing beam splitter 210. Semi-transparent reflection plane 212 reflects light beams $250_1$ and $252_1$ toward relay lens assembly 230.

Relay lens assembly 230, together with polarizing beam splitter 210, produces an inverted image of telescope entrance pupil 218 at the pupil of annular mirror 232. Bright-field light beam $250_1$ passes through the aperture of annular mirror 232 toward bright-field detector 234. Bright-field detector 234 receives bright-field light beam $250_1$ and detects properties thereof. Annular mirror 232 reflects gray-field light beam $252_1$ toward gray-field detector 236. Gray-field detector 236 receives gray-field light beam $252_1$ and detects properties thereof.

With reference to FIG. 4B, Illuminating light beam $244_2$ travels a path similar to illuminating light beam $244_1$, but on the opposite side of optical axis 260. Objective lens 226 focuses illuminating light beam $244_2$ onto a point $230_2$ on wafer surface 202, located on the opposite side of optical axis 260 from $230_1$, thereby producing a bright-field light beam $250_2$ and a gray-field light beam $252_2$. Bright-field light beam $250_2$ and gray-field light beam $252_2$, complete a similar path as bright-field light beam $250_1$ and gray-field light beam $252_1$, respectively, but on the opposite sides of optical axes 260, 262 and 264.

Scanner 206 may also emit intermediate illuminating light beams (not shown) at intermediate moments in time (i.e., between the emission of illuminating light beams $244_1$ and $244_2$). The intermediate illuminating light beams complete a similar path as illuminating light beams $244_1$ and $244_2$, but at intermediate angles relative to first optical axis 260. Thus, intermediate illuminating light beams reach intermediate points (not shown) on wafer surface 202 between points $230_1$ and $230_2$. Intermediate bright-field and gray-field light beams (not shown) are detected at bright-field detector 234 and gray-field detector 236, respectively, at intermediate moments in time.

Thus, system 200 (FIG. 3) scans the line between points $230_1$ and $230_2$ also known as the scan line, on wafer surface 202. The scan line length $L_1$ is approximately equal to $2 \times F \times \theta_1$.

The numerical aperture $NA_{BF1}$ of bright-field light beam $250_1$, also known as the bright-field numerical aperture, is equal to $$\frac{D_{BF1}}{2F},$$

wherein $D_{BF1}$ is the diameter of bright-field light beam $250_1$ and F is the focal length of objective lens 226. It is noted that bright-field light beams $250_1$ and $250_2$, and intermediate bright-field light beams in system 200, all have the same diameter $D_{BF1}$, and hence all have the same numerical aperture $NA_{BF1}$.

The numerical aperture $NA_{GF1}$ of gray-field light beam $252_1$, also known as the gray-field numerical aperture, is equal to $$\frac{D_{GF1}}{2F},$$

wherein $D_{GF1}$ is the outer diameter of gray-field light beam $252_1$ and F is the focal length of objective lens 226. It is noted that gray-field light beams $252_1$ and $252_2$, and intermediate gray-field light beams in system 200, all have the same outer diameter $D_{GF1}$, and hence all have the same numerical aperture $NA_{GF1}$.

System 200 may further include other telescopes (not shown) in addition to telescope 216. Some of these telescopes shall be described herein below in conjunction with FIGS. 4D and 4E. Each telescope has a different magnification. The telescopes are mounted on a turret, a slide (both not shown), and the like, which enables interchanging telescopes. Thus, system 200 can operate at different modes of operation, wherein each mode of operation is characterized by a different magnification.

Figure 4D:
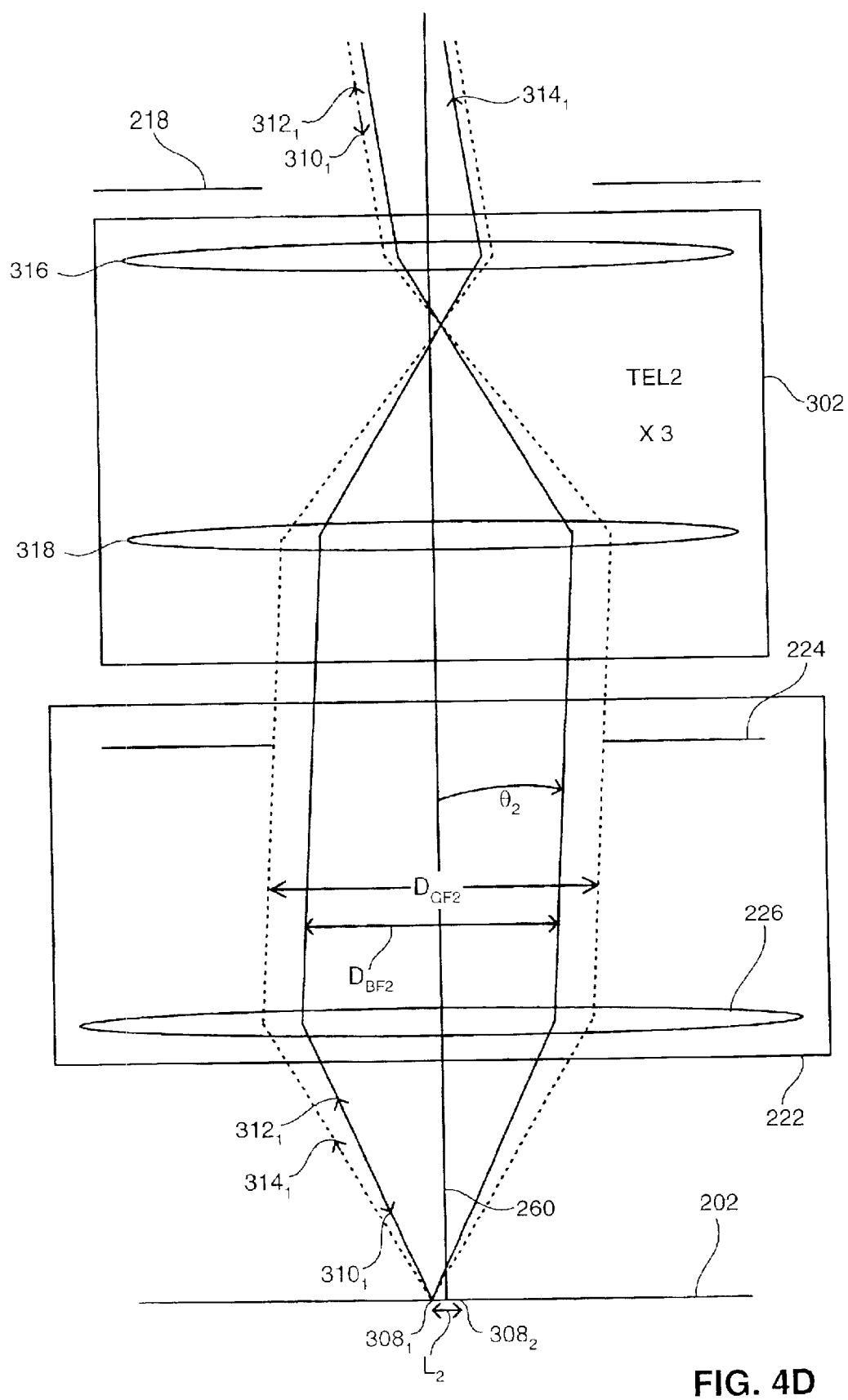
FIG. 4D is an illustration in detail of the aperture stop and objective lens assembly of system 200, another telescope replacing the telescope of FIG. 4A and used in another mode of operation of the system of FIG. 3A, and scanned wafer surface.
Figure 4E:
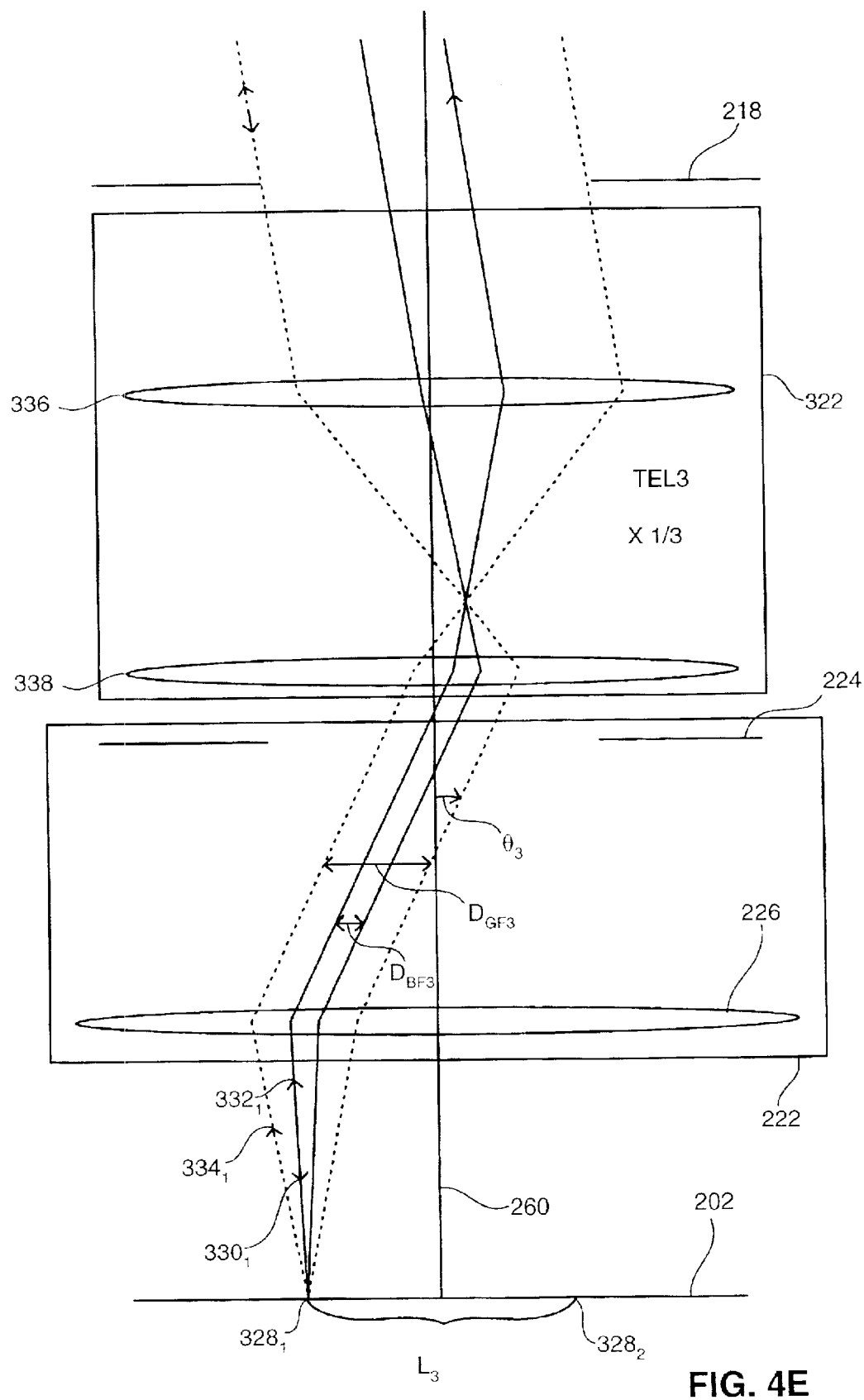
FIG. 4E is an illustration in detail of the aperture stop and objective lens assembly of the system of FIG. 3A, a further telescope, replacing the telescope of FIG. 4a and used in a further mode of operation of the system of FIG. 3a, and scanned wafer surface.

Reference is now made to FIGS. 4D and 4E. FIG. 4D is an illustration in detail of the aperture stop 218 and objective lens assembly 222 of system 200, a telescope 302, replacing telescope 216 and used in another mode of operation of system 200, and scanned wafer surface 202 (FIG. 3). FIG. 4E is an illustration in detail of the aperture stop 218 and objective lens assembly 222 of system 200, a telescope 322, replacing telescope 216 and used in a further mode of operation of system 200, and scanned wafer surface 202.

With reference to FIG. 4D, telescope 302 includes a first telescope lens 316 and a second telescope lens 318. The focal length of first telescope lens 316 is 3 times greater than the focal length of second telescope lens 318.

Telescope 302 receives an illuminating light beam $310_1$ at telescope entrance pupil 304. It is noted that illuminating light beam $310_1$ has an identical illumination path (not shown) in system 200 (FIG. 3), between scanner 206 and aperture stop 218, as illuminating light beam $244_1$ (FIG. 3). The diameter of illuminating light beam $310_1$ is also equal to $D_{IL}$.

Telescope 302 produces an inverted image of the pupil of aperture stop 218, at the pupil of objective aperture stop 224, at a magnification ratio M=3. Telescope 302 emits illuminating light beam $310_1$ at a diameter $D_{BF2}$, and an angle $\theta_2$. The linear magnification and the angular magnification of telescope 302 are 3 and ⅓, respectively. Accordingly, $D_{BF2} = 3 \times D_{IL}$, and $\theta_2 = \frac{1}{3} \times \theta_{IL}$.

Objective lens assembly 222 focuses illuminating light beam $310_1$ onto a point $308_1$, thereby producing a bright-field light beam $312_1$ and a gray-field light beam $314_1$. Bright-field hlight beam $312_1$ and gray-field light beam $314_1$ have diameters $D_{BF2}$ and $D_{GF2} = D_{TS}$, respectively.

The diameter $D_{BF2}$ of bright-field light beam $312_1$ is equal to $3 \times D_{IL}$. Accordingly, $D_{BF2}=3 \times D_{BF1}$, and hence, the bright-field numerical aperture $NA_{BF2}$ for the mode of operation of system 200, illustrated in FIG. 4D, is equal to $3 \times NA_{BF1}$. The diameter $D_{GF2}$ of gray-field light beam $314_1$ is equal to $D_{OS}=D_{TS}$, and hence, the gray-field numerical aperture $NA_{GF2}$ for this mode of operation is equal to $NA_{GF1}$.

The scan line length $L_2$ for the mode of operation of system 200, illustrated in FIG. 4B is approximately equal to $2 \times F \times \theta_2$ or, equivalently, $L_2 = \frac{1}{3} \times L_1$.

With reference to FIG. 4E, telescope 322 has a linear magnification of $M=\frac{1}{3}$. Telescope 322 includes a first telescope lens 336 and a second telescope lens 338. The focal length of first telescope lens 336 is 3 times less than the focal length of second telescope lens 338.

Telescope 322 receives an illuminating light beam $330_1$ at telescope entrance pupil 324. Telescope 322 produces an inverted image of pupil 324 at the pupil of objective aperture stop 224, at a magnification ratio $M=\frac{1}{3}$. Telescope 322 emits light beam $330_1$ at a diameter $D_{BF3}$, and an angle $\theta_3$. The linear magnification and the angular magnification of telescope 302 are $\frac{1}{3}$ and 3, respectively. Accordingly, $D_{BF3}=\frac{1}{3} \times D_{IL}$, and $\theta_3 = 3 \times \theta_{IL}$.

Objective lens assembly 222 focuses illuminating light beam $330_1$ onto a point $328_1$, thereby producing a bright-field light beam $322_1$ and a gray-field light beam $334_1$. Bright-field light beam $322_1$ has a diameter $D_{BF3}=\frac{1}{3} \times D_{BF1}$, and hence, the bright-field numerical aperture $NA_{BF3}$ for this mode of operation is equal to $\frac{1}{3} \times NA_{BF1}$. Gray-field light beam $334_1$ has a diameter $D_{GF3}=\frac{1}{3} \times D_{TS}=\frac{1}{3} \times D_{GF1}$, and hence, the gray-field numerical aperture $NA_{BF3}$ for this mode of operation is equal to $\frac{1}{3} \times NA_{GF1}$. It is noted that in the mode of operation of FIG. 4E, aperture stop 218 determines the diameter of gray-field light beam $334_1$.

The scanning resolution for system 200 is highly correlated with the gray-field numerical aperture and to the bright-field numerical aperture. In addition, the scanning speed of system 200 is proportional to the scan line length. Thus, by selecting different modes of operation using different telescopes, the user of system 200 can choose between a low-resolution, high-speed scan, a high-resolution, low-speed scan and other modes in between.

System 200 uses a single (i.e., non interchangeable) objective lens assembly together with a plurality of interchangeable telescopes, for the common illumination and collection path, as opposed to conventional systems which use a different objective lens assembly for each magnification.

It is noted that a combination of a single high NA objective lens and a plurality of telescopes, provides a large collection area (i.e., for collecting a collected light beam having a large diameter), at a relatively low cost, compared with that of a plurality of objective lens assemblies which are designed to exhibit that same large collection area. It is further noted that using an objective lens assembly having a high numerical aperture, provides a larger gray-field light beam, and hence, provides more information to the gray-field detector.

It is still further noted that the use of interchangeable telescopes instead of interchangeable objective lens assemblies, reduces the chance for contamination of the wafer, since the telescopes are isolated from the wafer, whereas the objective lens assembly is the element of the optical system closest to the wafer and further not isolated there from.

According to another aspect of the disclosed technique, there is provided novel optical structure for separating gray-field and bright-field light beams. According to this aspect, the combined light beam arrives first at an annular mirror, which separates there between. The annular mirror reflects the gray-field light beam to a gray-field detector and lets the bright-field light beam pass there through, toward a quarter wave plate and polarizing beam splitter.

Figure 5:
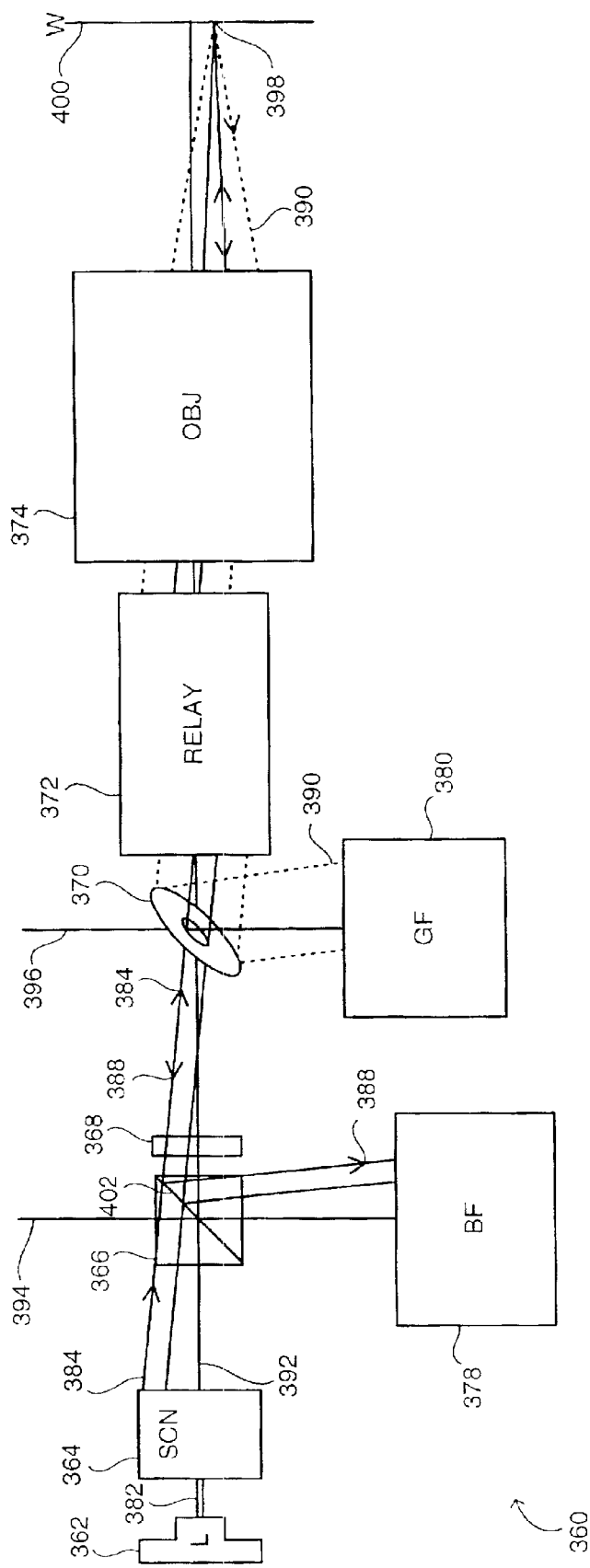
FIG. 5 is a schematic illustration of a scanning system constructed and operative in accordance with another embodiment of the disclosed technique.

Reference is now made to FIG. 5, which is a schematic illustration of a scanning system, generally referenced 360, constructed and operative in accordance with another embodiment of the disclosed technique.

In the example set forth in FIG. 5, system 360 is used for scanning a wafer surface 400. System 360 includes a laser light source 362, a scanner 364, a polarizing beam splitter 366, a quarter wave plate 368, an annular mirror 370, a relay lens assembly 372, an objective lens assembly 374, a bright-field detector 378 and a gray-field detector 380. Objective lens assembly 374 includes an objective aperture stop 376. Polarizing beam splitter 366 includes a semi-transparent reflection plane 402.

Laser light source 362, scanner 364, polarizing beam splitter 366, quarter wave plate 368, annular mirror 370, relay lens assembly 372, objective lens assembly 374 and wafer surface 400 are positioned along a first optical axis 392. First optical axis 392 is perpendicular to wafer surface 400. Scanner 364 is positioned between laser 362 and polarizing beam splitter 366. Quarter wave plate 368 is positioned between polarizing beam splitter 366 and annular mirror 370. Relay lens assembly 372 is positioned between annular mirror 370 and objective lens assembly 374. Objective lens assembly 374 is positioned between relay lens assembly 372 and wafer surface 400.

Polarizing beam splitter 366 and bright-field detector 378 are positioned along a second optical axis 394. In the present example, second optical axis 394 is perpendicular to first optical axis 392.

Annular mirror 370 and gray-field detector 380 are positioned along a third optical axis 396. In the present example, third optical axis 396 is parallel to second optical axis 394.

Laser light source 362, scanner 364, polarizing beam splitter 366, semi-transparent reflection plane 402, quarter wave plate 368, annular mirror 370, relay lens assembly 372, objective lens assembly 374, objective entrance pupil 376, bright-field detector 378 and gray-field detector 380 are generally similar to laser light source 204, scanner 206, polarizing beam splitter 210, semi-transparent reflection plane 212, quarter wave plate 214, annular mirror 232, relay lens assembly 230, objective lens assembly 222, objective aperture stop 224, bright-field detector 234 and gray-field detector 236 (FIG. 3), respectively.

Laser light source 362 emits a laser light beam 382 toward scanner 364. Scanner 364 receives laser light beam 382 and emits an illuminating light beam 384 toward polarizing beam splitter 366. Illuminating light beam 384 passes through semi-transparent plane 402 and quarter wave plate 368, and from there, further through the aperture of annular mirror 370 toward relay lens assembly 372. Relay lens assembly 372 produces an inverted image of the pupil of annular mirror 370, at the entrance pupil of objective lens assembly 374.

Objective lens assembly 374 focuses illuminating light beam 388 onto a point 398 on wafer surface 400, thereby producing a bright-field light beam 388 and a gray-field light beam 390. Objective lens assembly 374 collects and collimates light beams 388 and 390, and directs light beams 388 and 390 toward relay lens assembly 372.

Relay lens assembly 376 produces an inverted image of the entrance pupil of objective lens assembly 374 at the pupil annular mirror 370. Annular mirror 370 reflects gray-field light beam 390 toward gray-field detector 380. Gray-field detector 380 receives gray-field light beam 390 and detects properties thereof.

Bright-field light beam 388 passes through the aperture of annular mirror 370 and from there, further through quarter wave plate 368, towards polarizing beam splitter 366. Semi-transparent reflection plane 402 reflects bright-field light beam 388 toward bright-field detector 378. Bright-field detector 378 receives bright-field light beam 388 and detects properties thereof.

Polarizing beam splitter 366 and quarter wave plate 368 are used in system 360 for reflecting bright-field light beam 388, and not for reflecting gray-field light beam 390. Thus, a smaller polarizing beam splitter and a smaller quarter wave plate can be used in system 360, since the required sizes of polarizing beam splitter 366 and quarter wave plate 368 are determined by the bright-field diameter and scanning angle, and not by the gray-field diameter. It is noted that the use of a smaller polarizing beam splitter and a smaller quarter wave plate significantly reduces the manufacturing cost of system 360, since the cost and size of the polarizing beam splitter are highly correlated there between.

According to another aspect of the disclosed technique, apodizators are positioned in the illumination path (and not in the collection path), thereby controlling the shape of the illumination light beams, without directly affecting the shape of the respective collected bright-field and gray-field light beams. It is noted that the shape of the collected light beams may be indirectly affected by the apodizators, since the collected light beams depend on the respective illuminated light beams. According to this aspect, the illuminating light beam first passes through an apodizator located at a first pupil. The apodizator shapes the illuminating light beam at a predetermined shape. The illuminating light beam then passes through a relay lens assembly, which produces an image of the first pupil at the entrance pupil of the objective lens.

Figure 6:
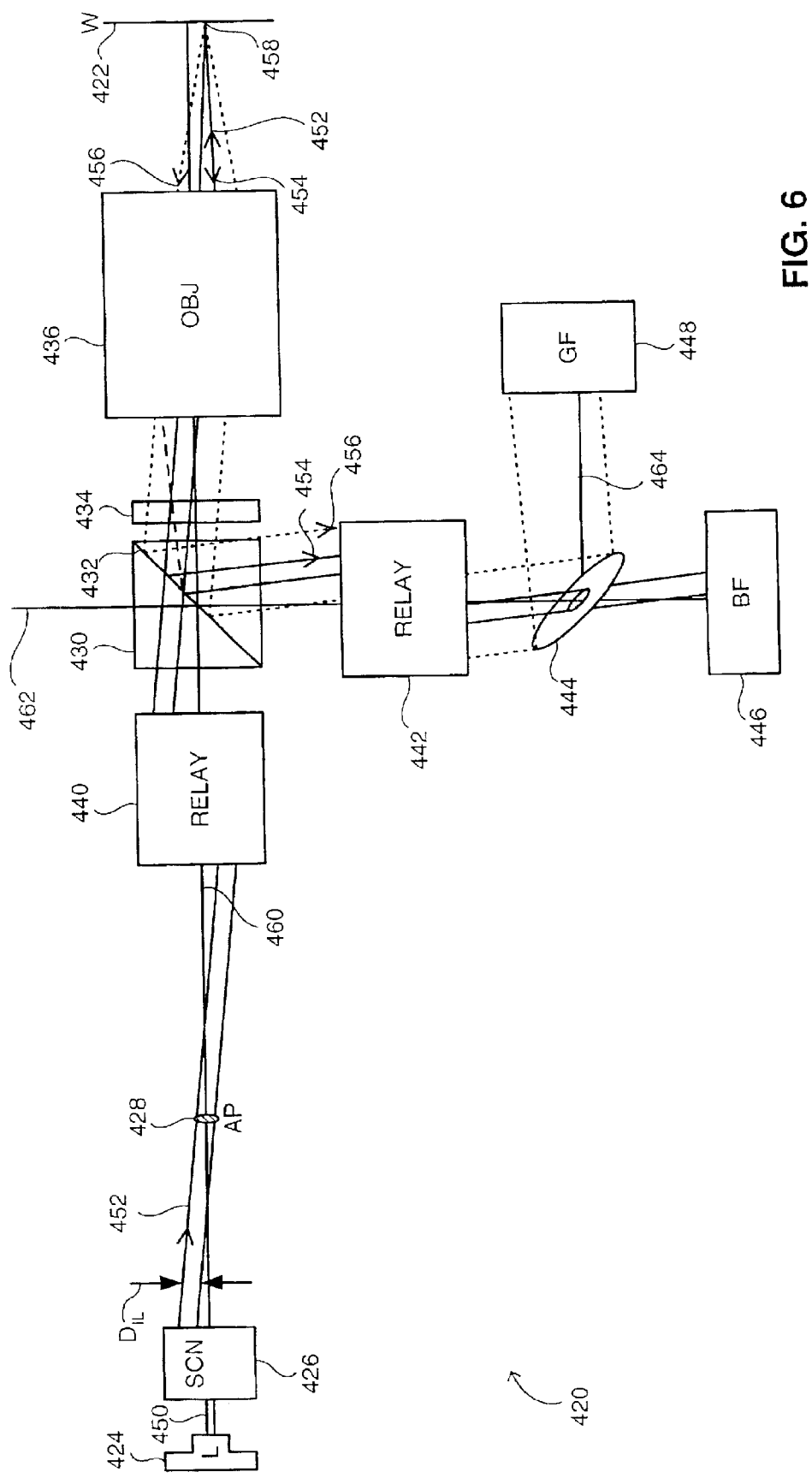
FIG. 6 is a schematic illustration of a scanning system using apodizators, constructed and operative in accordance with a further embodiment of the disclosed technique.

Reference is now made to FIG. 6, which is a schematic illustration of a scanning system, generally referenced 420, constructed and operative in accordance with another embodiment of the disclosed technique.

In the example set forth in FIG. 6, system 420 is used for scanning a wafer surface 422. System 420 includes a laser light source 424, a scanner 426, an apodizator 428, a polarizing beam splitter 430, a quarter wave plate 434, an objective lens assembly 436, relay lens assemblies 440 and 442, an annular mirror 444, a bright-field detector 446 and a gray-field detector 448. Objective lens assembly 436 includes an objective entrance pupil 438 and an objective lens 466. Polarizing beam splitter 430 includes a semi-transparent reflection plane 432. Laser light source 424, scanner 426, apodizator 428, relay lens assembly 440, polarizing beam splitter 430, quarter wave plate 434, objective lens assembly 436 and wafer surface 422 are positioned along a first optical axis 460. First optical axis 460 is perpendicular to wafer surface 422. Scanner 426 is positioned between laser light source 424 and apodizator 428. Relay lens assembly 440 is positioned between apodizator 428 and polarizing beam splitter 430. Quarter wave plate 434 is positioned between polarizing beam splitter 432 and objective lens assembly 436. Objective lens assembly 436 is positioned between quarter wave plate 434 and wafer surface 422.

Polarizing beam splitter 430, relay lens assembly 442, annular mirror 444 and bright-field detector 446 are positioned along a second optical axis 462. In the present example, second optical axis 462 is perpendicular to first optical axis 460. Relay lens assembly 442 is positioned between polarizing beam splitter 430 and annular mirror 444. Annular mirror 444 is positioned between relay lens assembly 442 and bright-field detector 446.

Annular mirror 444 and gray-field detector 448 are positioned along a third optical axis 464. In the present example, third optical axis 464 is parallel to first optical axis 460.

Laser light source 424, scanner 426, polarizing beam splitter 430, semi-transparent reflection plane 432, quarter wave plate 434, annular mirror 444, objective lens assembly 436, objective entrance pupil 438, bright-field detector 446 and gray-field detector 448 are generally similar to laser light source 204, scanner 206, polarizing beam splitter 210, semi-transparent reflection plane 212, quarter wave plate 214, annular mirror 232, objective lens assembly 222, objective aperture stop 224, bright-field detector 234 and gray-field detector 236 (FIG. 3), respectively. Relay lens assemblies 440 and 442 are generally similar to relay lens 230 (FIG. 3).

In general, apodizator 428 has a minimal diameter of at least $D_{IL}$. In the present example, apodizator 428 is circular and has a diameter of $D_{IL}$. A first portion of the area of apodizator 428 is transparent, while a second portion is opaque. For example, apodizator 428 may include a transmitting outer annular region and an opaque inner circular region. Thus, apodizator 428 shapes light beams incident there upon.

Annular mirror 444 is located at a pupil of the scanning system. In the present example, annular mirror 444 is oriented at 45 degrees relative to axes 462 and 464. Semi-transparent reflection plane 432 is oriented at 45 degrees relative to optical axes 460 and 462.

Laser light source 424 emits a laser light beam 450 toward scanner 426. Scanner 426 receives laser light beam 450 and emits an illuminating light beam 452, at diameter $D_{IL}$, toward apodizator 428.

Apodizator 428 shapes illuminating light beam 452$_1$ at a predetermined light beam shape.

Illuminating light beam 452 then reaches relay lens assembly 440. Relay lens assembly 440 produces an inverted image of the pupil of apodizator 428, at the entrance pupil of objective lens assembly 436. Illuminating light beam 452 proceeds from relay lens assembly 440 to polarizing beam splitter 430. Illuminating light beam 452 passes through polarizing beam splitter and from there, further through quarter wave plate 434 toward objective lens assembly 436. Objective lens assembly 436 focuses illuminating light beam 452 onto a point 458 on wafer surface 400, thereby producing a bright-field light beam 454 and a gray-field light beam 456. Objective lens assembly 436 collects light beams 454 and 456, and directs them towards quarter wave plate 434. Light beams 454 and 456 pass through quarter wave plate 434 and are reflected from semi-transparent reflection plane 432, toward relay lens assembly 442. Relay lens assembly 442 produces an inverted image of the entrance pupil of objective lens assembly 436, at the pupil of annular mirror 444. Bright-field light beam 454 passes through the aperture of annular mirror 444 and is detected at bright-field detector 446. Gray-field light beam 456 is reflected by annular mirror 464 and is detected at gray-field detector 448.

System 420 may further include more apodizators (not shown) in addition to apodizator 428. Each apodizator has different transmitting portions with different shapes or dimensions, and hence, each apodizator determines a different shape for the illuminating light beam. The apodizators are mounted on a turret, a slide (both not shown), and the like, which enables interchanging apodizators. Thus, system 420 can operate at different modes of operation, wherein each mode of operation is characterized by different light beam shape, depending on the selected apodizator.

Figure 7A:
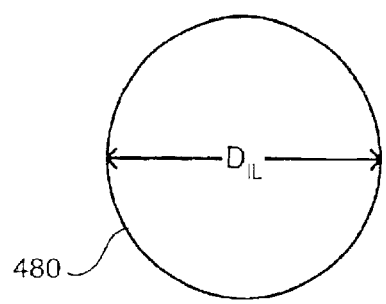
FIG. 7A is a schematic illustration of an apodizator constructed and operative in accordance with an embodiment of the disclosed technique.
Figure 7B:
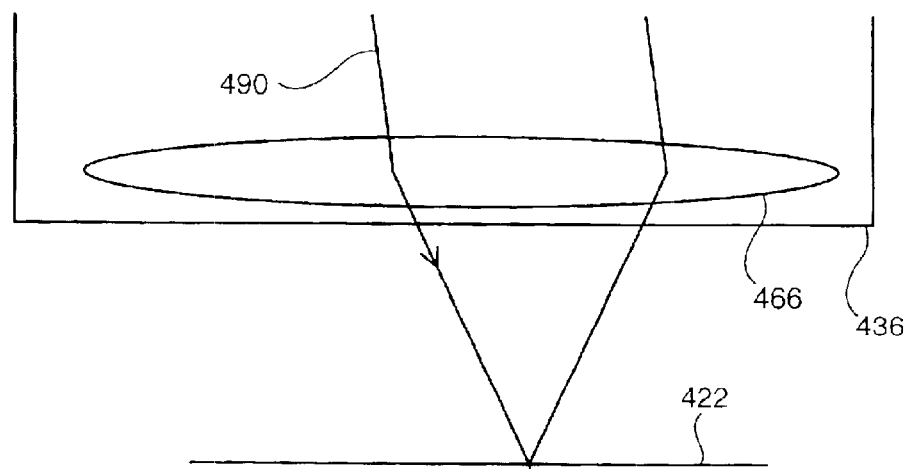
FIG. 7B is a schematic illustration of the objective lens assembly and the scanned wafer surface of FIG. 6, and an illuminating light beam which has already passed through the apodizator of FIG. 7A.
Figure 7C:
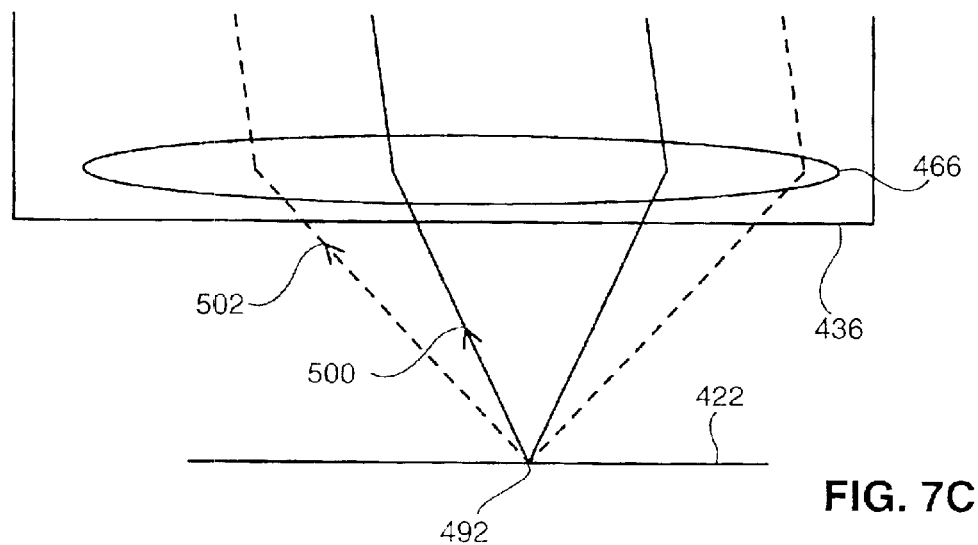
FIG. 7C is a schematic illustration of a bright-field light beam and a gray-field light beam, which are reflections and refractions of illuminating light beam of FIG. 7B, by the wafer surface, traveling from the scanned wafer surface and passing through the objective lens assembly of the system of FIG. 6.

Reference is further made to FIGS. 7A, 7B and 7C. FIG. 7A is a schematic illustration of an apodizator 480, constructed and operative in accordance with a further embodiment of the disclosed technique. FIG. 7B is a schematic illustration of objective lens assembly 436 of system 420, scanned wafer surface 422 (FIG. 6), and an illuminating light beam 490, which has already passed though apodizator 480 (FIG. 7A). FIG. 7C is a schematic illustration of a bright-field light beam 500 and a gray-field light beam 502, which are reflections and refractions of illuminating light beam 490 (FIG. 7B), by wafer surface 422, traveling from wafer surface 422 and passing through objective lens assembly 436 (FIG. 6).

With reference to FIG. 7A, apodizator 480 is a circular, transparent filter. Apodizator 480 has diameter $D_{IL}$. Apodizator 480 is uniform (i.e., fully transparent or filtering at specific wavelengths, and the like) and as such affects illuminating light beam 490 in a uniform spatial manner.

With reference to FIG. 7B, objective lens assembly 436 includes an objective lens 466. Illuminating light beam 490 illuminates a point 492 on wafer surface 422, after passing through apodizator 480 (FIG. 7A).

With reference to FIG. 7C, wafer surface 422 scatters and reflects light from point 492, thereby producing a bright-field light beam 500 and a gray-field light beam 502. Light beams 500 and 502 are eventually detected at bright-field detector 446 and gray-field detector 448 (FIG. 6), respectively.

Figure 8A:
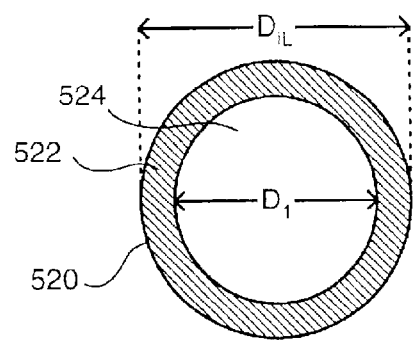
FIG. 8A is a schematic illustration of another apodizator, constructed and operative in accordance with another preferred embodiment of the disclosed technique.
Figure 8B:
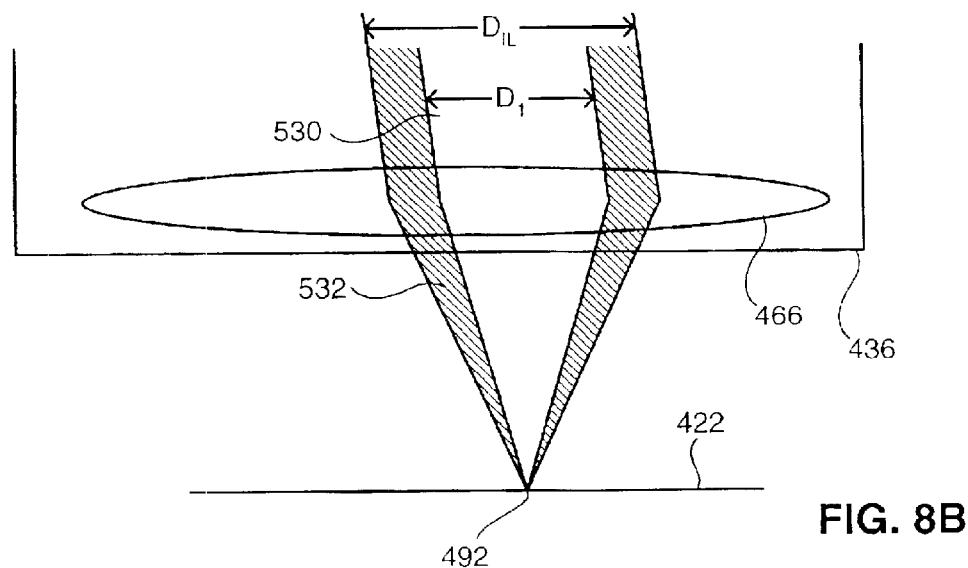
FIG. 8B is a schematic illustration of the objective lens assembly and the scanned wafer surface of FIG. 6, and an illuminating light beam which has already passed through the apodizator of FIG. 8A.
Figure 8C:
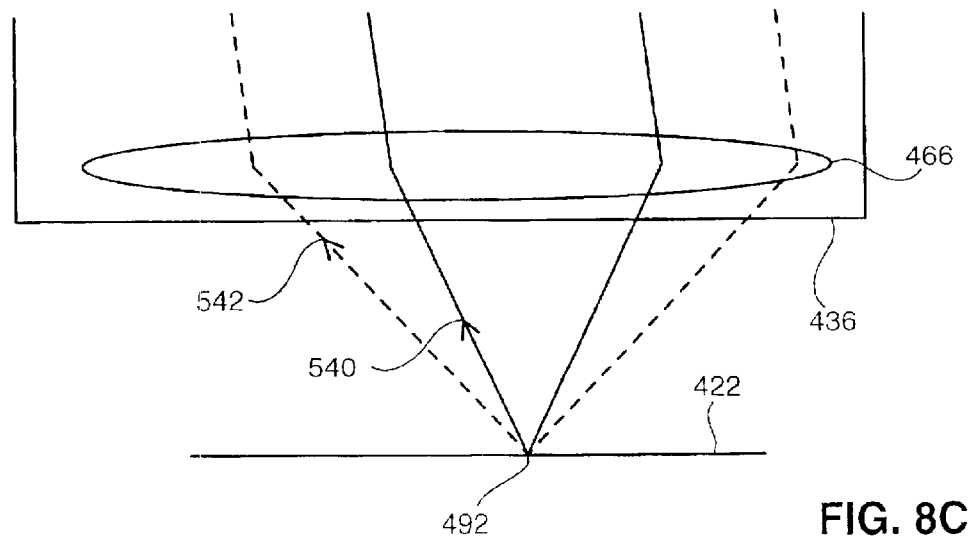
FIG. 8C is a schematic illustration of a bright-field light beam and a gray-field light beam, which are reflections and refractions of illuminating of the illuminating light beam of FIG. 8B, by the wafer surface, traveling from the scanned wafer surface and passing through the objective lens assembly of the system of FIG. 6.

Reference is further made to FIGS. 8A, 8B and 8C. FIG. 8A is a schematic illustration of another apodizator 520, constructed and operative in accordance with another embodiment of the disclosed technique. FIG. 8B is a schematic illustration of objective lens assembly 436 of system 420, scanned wafer surface 422 (FIG. 6), and an illuminating light beam 530, which has already passed through apodizator 520 (FIG. 8A). FIG. 8C is a schematic illustration of a bright-field light beam 540 and a gray-field light beam 542, which are reflections and refractions of illuminating light beam 530 (FIG. 8B), by wafer surface 422, traveling from wafer surface 422 and passing through objective lens assembly 436 (FIG. 6).

With reference to FIG. 8A, apodizator 520 is a circular filter having diameter $D_{IL}$. Apodizator 520 includes an outer region 522 and an inner region 524. Outer region 522 is opaque and annular, limited by outer diameter $D_{IL}$ and an inner diameter $D_1$, wherein $D_1 < D_{IL}$. Inner region 524 is transparent and circular, having diameter $D_1$.

With reference to FIG. 8B, illuminating light beam 530 illuminates point 492 on wafer surface 422, after passing through apodizator 520 (FIG. 8A). Illuminating light beam 530 has diameter $D_1$. A volume 532 (shaded) around illuminating light beam 530, would have been a part of illuminating light beam 532, had it not been blocked by outer region 522 of apodizator 520 (FIG. 8A). The cross-section of volume 532 is annular, limited between inner diameter $D_1$ and outer diameter $D_{IL}$. It is noted that the diameters of light beam 530 and volume 532, and some of the other light beams in the description that follows, refer to the diameter when the light beam is collimated.

With reference to FIG. 8C, wafer surface 422 scatters and reflects illuminating light beam 530 (FIG. 8B), thereby producing a bright-field light beam 540 and a gray-field light beam 542. Light beams 540 and 542 are eventually detected at bright-field detector 446 and gray-field detector 448 (FIG. 6), respectively.

Figure 9A:
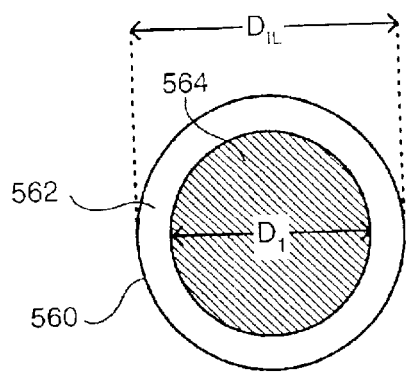
FIG. 9A is a schematic illustration of another apodizator, constructed and operative in accordance with a further embodiment of the disclosed technique.
Figure 9B:
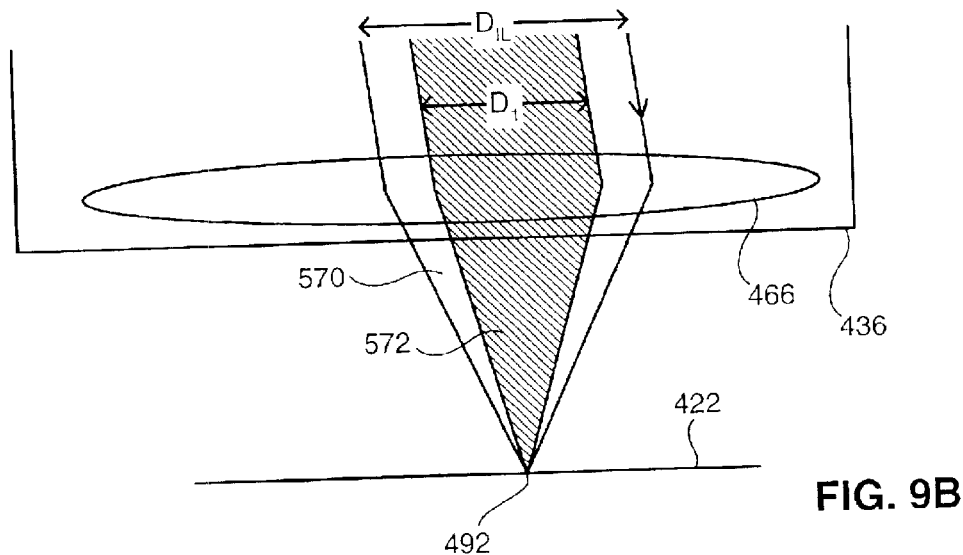
FIG. 9B is a schematic illustration of the objective lens assembly and the scanned wafer surface of FIG. 6, and an illuminating light beam which has already passed through the apodizator of FIG. 9A.
Figure 9C:
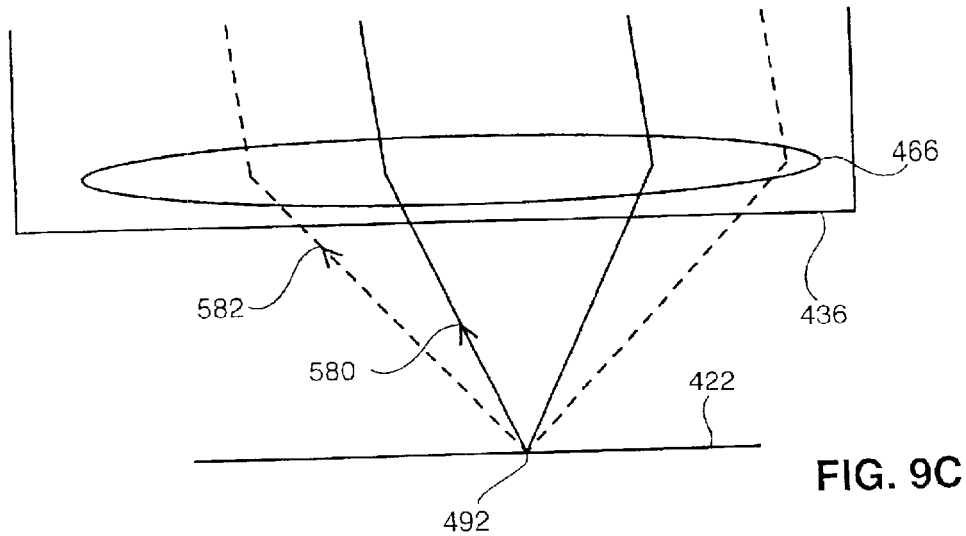
FIG. 9C is a schematic illustration of a bright-field light beam and a gray-field light beam, which are reflections and refractions of the illuminating light beam of FIG. 9B, by the wafer surface, traveling from the scanned wafer surface and passing through the objective lens assembly of the system of FIG. 6.

Reference is further made to FIGS. 9A, 9B and 9C. FIG. 9A is a schematic illustration of another apodizator 560, constructed and operative in accordance with a further embodiment of the disclosed technique. FIG. 9B is a schematic illustration of objective lens assembly 436 of system 420, scanned wafer surface 422 (FIG. 6), and an illuminating light beam 570, which has already passed through apodizator 560 (FIG. 9A). FIG. 9C is a schematic illustration of a bright-field light beam 580 and a gray-field light beam 582, which are reflections and refractions of illuminating light beam 570 (FIG. 9B), by wafer surface 422, traveling from wafer surface 422 and passing through objective lens assembly 436.

With reference to FIG. 9A, apodizator 560 is a circular filter having diameter $D_{IL}$. Apodizator 560 includes an outer region 562 and an inner region 564. Outer region 562 is transparent and annular, limited between outer diameter $D_{IL}$ and inner diameter $D_1$. Inner region 564 is opaque and circular, having diameter $D_1$.

With reference to FIG. 9B, illuminating light beam 570 illuminates point 492 on wafer surface 422. The cross-section of illuminating light beam 570 is annular, limited between outer diameter $D_{IL}$ and inner diameter $D_1$. Illuminating light beam 570 surrounds a volume 572 (shaded). Volume 572 has diameter $D_1$. Volume 572 would have been a part of illuminating light beam 570 had it not been blocked by inner region 564 of apodizator 560 (FIG. 9A). With reference to FIG. 9C, wafer surface 422 scatters and reflects illuminating light beam 570 (FIG. 9B), thereby producing bright-field light beam 580 and a gray-field light beam 582.

Figure 10A:
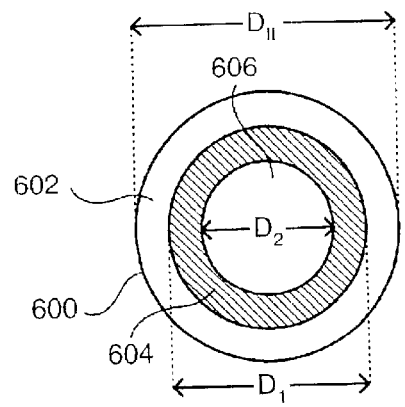
FIG. 10A is a schematic illustration of another apodizator, constructed and operative in accordance with another embodiment of the disclosed technique.
Figure 10B:
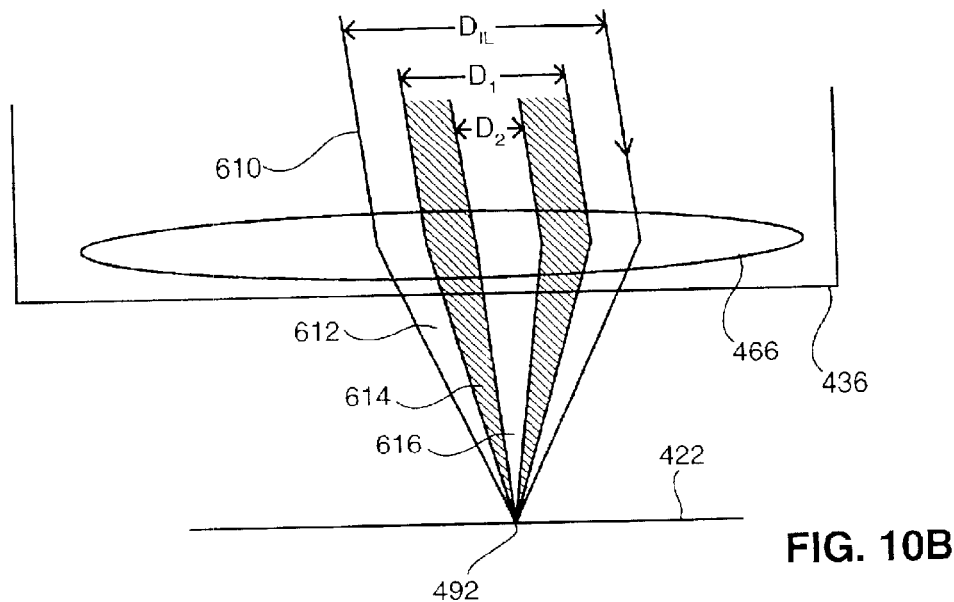
FIG. 10B is a schematic illustration of the objective lens assembly and the scanned wafer surface of FIG. 6, and an illuminating light beam which has already passed through the apodizator of FIG. 10A.
Figure 10C:
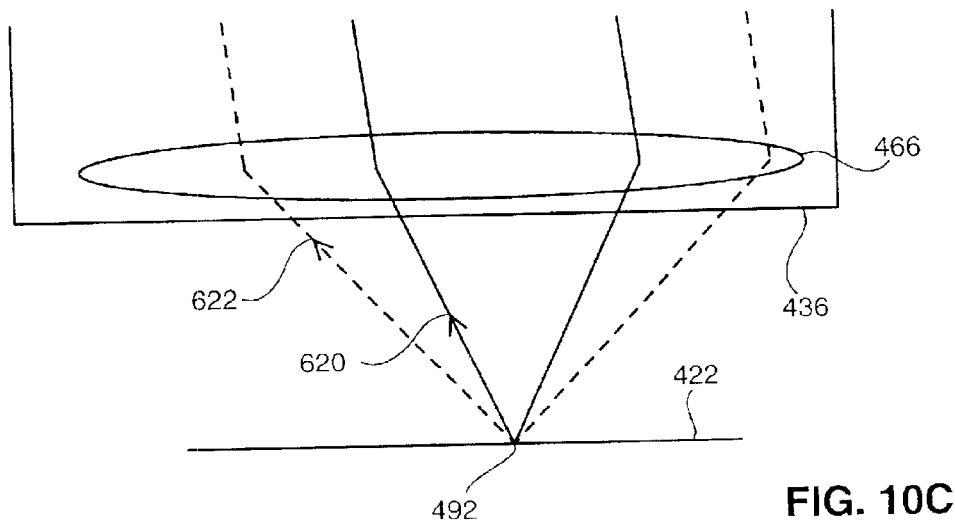
FIG. 10C is a schematic illustration of a bright-field light beam and a gray-field light beam, which are reflections and refractions of the illuminating light beam of FIG. 10B, by the wafer surface, traveling from the scanned wafer surface and passing through the objective lens assembly of the system of FIG. 6.

Reference is further made to FIGS. 10A, 10B and 10C. FIG. 10A is a schematic illustration of another apodizator 600, constructed and operative in accordance with another embodiment of the disclosed technique. FIG. 10B is a schematic illustration of objective lens assembly 436 of system 420, scanned wafer surface 422 (FIG. 6), and an illuminating light beam 610, which has already passed through apodizator 600 (FIG. 10A). FIG. 10C is a schematic illustration of a bright-field light beam 620 and a gray-field light beam 622, which are reflections and refractions of illuminating light beam 610 (FIG. 10B), by wafer surface 422, traveling from wafer surface 422 and passing through objective lens assembly 436.

With reference to FIG. 10A, apodizator 600 is a circular filter having diameter $D_{IL}$. Apodizator 600 includes an outer region 602, an intermediate region 604 and an inner region 606. Outer region 602 is transparent and annular, limited between outer diameter $D_{IL}$ and inner diameter $D_1$. Intermediate region 604 is opaque and annular, limited between outer diameter $D_1$ and an inner diameter $D_2$, wherein $D_2 < D_1 < D_{IL}$. Inner region 606 is transparent and circular, having diameter $D_2$.

With reference to FIG. 10B, illuminating light beam 610 illuminates point 492 on wafer surface 422. Illuminating light beam 610 has diameter $D_{IL}$. Illuminating light beam 610 includes an outer portion 612 and an inner portion 616. The cross-section of outer portion 612 is annular, limited between outer diameter $D_{IL}$ and inner diameter $D_1$. The cross-section of inner portion 616 is circular, having diameter $D_2$. A volume 614 surrounds inner portion 616. Outer portion 616 surrounds volume 614. The cross-section of volume 614 is annular, limited between outer diameter $D_1$ and inner diameter $D_2$. Volume 614 would have been a part of illuminating light beam 610, had it not been blocked by inner region 606 of apodizator 600 (FIG. 10A).

Figure 11A:
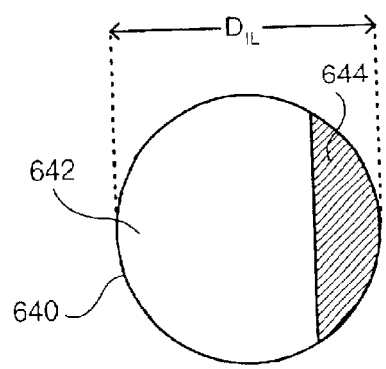
FIG. 11A is a schematic illustration of another apodizator constructed and operative in accordance with a further embodiment of the disclosed technique.
Figure 11B:
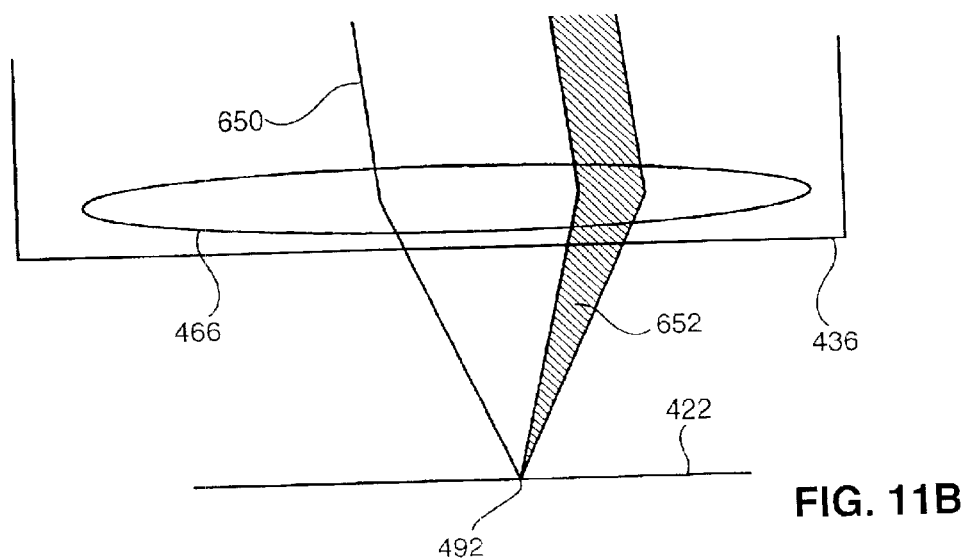
FIG. 11B is a schematic illustration of the objective lens assembly and the scanned wafer surface of FIG. 6, and an illuminating light beam which has already passed through the apodizator of FIG. 11A.
Figure 11C:
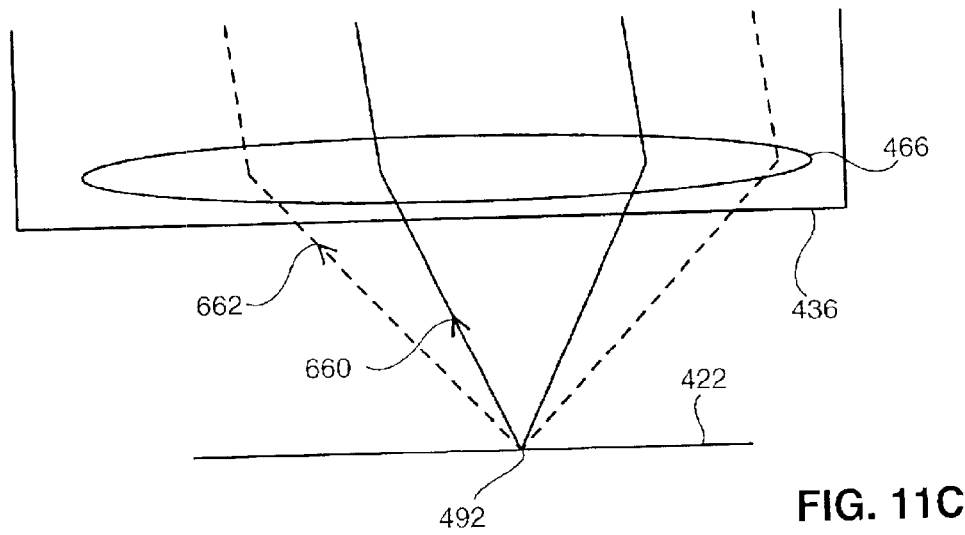
FIG. 11C is a schematic illustration of a bright-field light beam and a gray-field light beam, which are reflections and refractions of the illuminating light beam of FIG. 11B, by the wafer surface, traveling from the scanned wafer surface and passing through the objective lens assembly of the system of FIG. 6.

With reference to FIG. 10C, wafer surface 422 scatters and reflects illuminating light beam 610 (FIG. 10B), thereby producing a bright-field light beam 620 and a gray-field light beam 622. Reference is now made to FIGS. 11A, 11B and 11C. FIG. 11A is a schematic illustration of another apodizator, generally referenced 640, constructed and operative in accordance with a further embodiment of the disclosed technique. FIG. 11B is a schematic illustration of objective lens assembly 436 of system 420, scanned wafer surface 422 (FIG. 6), and an illuminating light beam 650, which has already passed through apodizator 640 (FIG. 11A). FIG. 11C is a schematic illustration of a bright-field light beam 660 and a gray-field light beam 662, which are reflections and refractions of illuminating light beam 650 (FIG. 11B), by wafer surface 422, traveling from wafer surface 422 and passing through objective lens assembly 436.

With reference to FIG. 11A, apodizator 640 is a circular filter having diameter $D_{IL}$. Filter 640 includes a left region 642 and a right region 644. Left region 642 is opaque. Right region 644 is transparent.

With reference to FIG. 11B, illuminating light beam 650 illuminates point 492 on wafer surface 422. A volume 652, would have been a part of illuminating light beam 650 had it not been blocked by right region 644 of apodizator 640 (FIG. 11A).

With reference to FIG. 11C, wafer surface 422 scatters and reflects illuminating light beam 650 (FIG. 11B), thereby producing a bright-field light beam 660 and a gray-field light beam 662. It is noted that light beams 500 and 502 (FIG. 7C), 540 and 542 (FIG. 8C), 580 and 582 (FIG. 9C), 620 and 622 (FIG. 10C), and 660 and 662 (FIG. 11C), all have the same diameters. However, these light beams generally differ in other properties, since their respective illuminating light beams are generally different.

Figure 12:
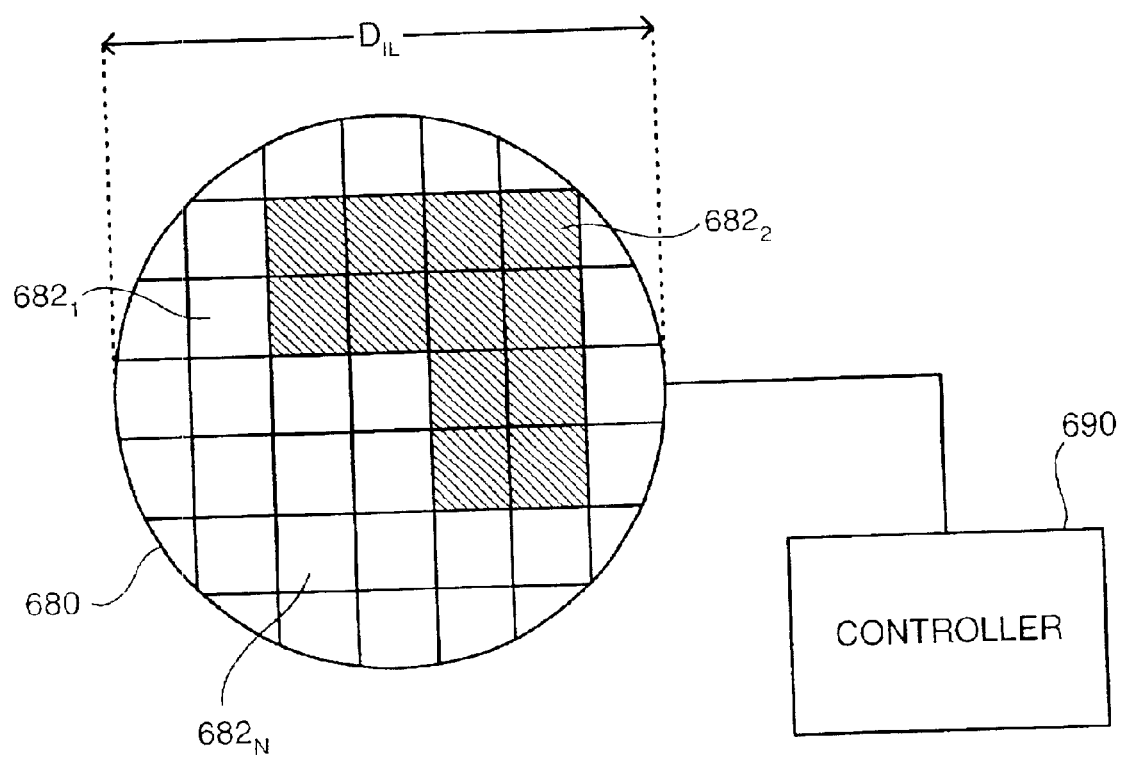
FIG. 12 is a schematic illustration of a dynamic apodizator, and a controller, constructed and operative in accordance with another embodiment of the disclosed technique.

Reference is now made to FIG. 12, which is a schematic illustration of a dynamic apodizator 680 and a controller 690, constructed and operative in accordance with a further embodiment of the disclosed technique.

Dynamic apodizator 680 is coupled to controller 690. It is noted that controller 690 may be further coupled with other elements of the scanning system, a user interface, a combination thereof, and the like. Dynamic apodizator 680 includes a plurality of light valve elements, generally referenced $680_i$, such as light valve elements $682_1$, $682_2$, and $682_N$, arranged in a two-dimensional array.

Light valve elements are components, which have an ability to influence light in at least one way. Some of these ways are, for example: scattering, converging, diverging, absorbing, imposing a polarization pattern, influencing a polarization pattern which, for example, may be by rotation of a polarization plane, influencing wave length, diverting a beam's direction for example by using digital micro-mirror display (also known as DMD) or by using field effect, influencing phase, interference techniques, which either blocks or transfers a portion of beam of light and the like. Activation of light valve elements, which are utilized by the disclosed technique, can be performed either electrically, magnetically or optically. Commonly used light valve elements are liquid crystal based elements, which either rotate or create and enforce a predetermined polarization axis. In the example set forth in FIG. 12, light valve elements $680_i$ have two states, transmitting and non-transmitting. A light valve in the transmitting state, transmits light there through, and hence, light incident there upon reaches bright-field detector 446 (FIG. 6). A light valve in the non-transmitting state prevents light from reaching bright-field detector 446.

Depending on a signal from controller 690 to dynamic apodizator 680, each of light valves $680_i$ is either transparent or opaque. In the present example, light valve elements $682_1$ and $682_N$ are transparent, and cell $682_2$ is opaque.

According to another aspect of the disclosed technique, system 420 (FIG. 6) is complemented by bright-field filters, which block a selected portion of the bright-field light beam before the bright-field light beam reaches the bright-field detector.

Figure 13A:
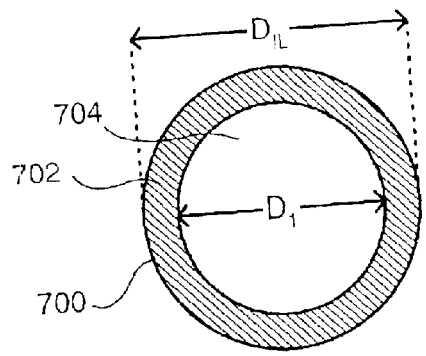
FIG. 13A is a schematic illustration of a bright-field filter.
Figure 13B:
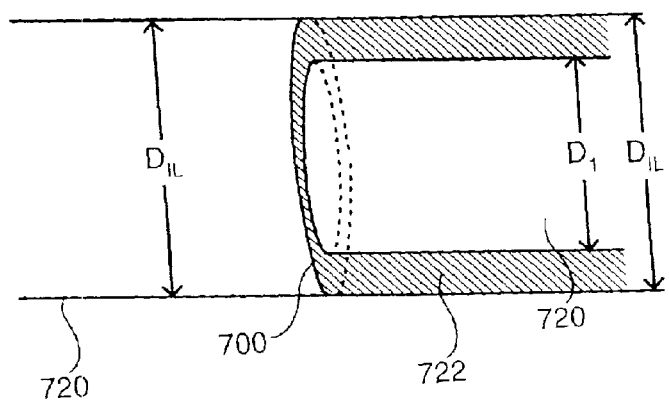
Figure 13C:
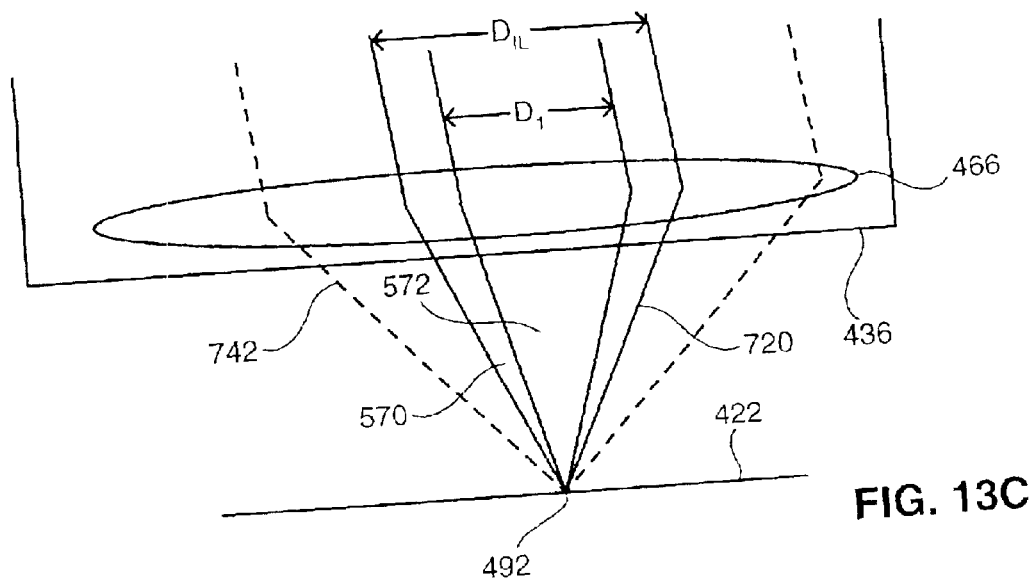
FIG. 13C is a schematic illustration of the objective lens assembly of the system of FIG. 6, the scanned wafer surface, the illuminating light beam of FIG. 9A, and the bright-field light beam of FIG. 13B and a gray field light beam, which are reflections and refractions of the illuminating light beam from the wafer surface of FIG. 6.

Reference is now made to FIGS. 13A, 13B and 13C. FIG. 13A is a schematic illustration of a bright-field filter 700. FIG. 13B is a schematic illustration of bright-field filter 700 (FIG. 13A) and a bright-field light beam 720 incident there upon and partially transmitted there through. FIG. 13C is a schematic illustration of objective lens assembly 436 of system 420 and scanned wafer surface 422 (FIG. 6), illuminating light beam 570 and volume 572 (FIG. 9A), and bright-field light beam 720 (FIG. 13B) and a gray-field light beam 742, which are reflections and refractions of illuminating light beam 720, by wafer surface 422.

With reference to FIG. 13A, bright-field filter 700 is a circular filter having diameter $D_{IL}$. Bright-field filter 700 includes an outer region 702 and an inner region 704. Outer region 702 is opaque and annular, limited between outer diameter $D_{IL}$ and inner diameter $D_1$. Inner region 704 is transparent and circular, having diameter $D_1$.

With reference to FIG. 13B, bright-field light beam 720 reaches bright-field filter 700 at diameter $D_{IL}$. Bright field light beam is partially transmitted through bright-field filter 700 at diameter $D_1$. A volume 722 (shaded) around bright-field light beam 720, would have been a part of bright-field light beam 720 had it not been blocked by outer region 702 of bright-field filter 700 (FIG. 13A). The cross-section of volume 722 is annular, limited between inner diameter $D_1$ and outer diameter $D_{IL}$.

With reference to FIG. 13C, objective lens assembly 436 focuses illuminating light beam 570 onto a point 492 on wafer surface 422. Wafer surface 422 scatters and reflects illuminating light beam 570, thereby producing bright-field light beam 720 (FIG. 13B) and gray-field light beam 742. Volume 572 is a part of bright-field light beam 720. As mentioned above, volume 572 would have been a part of illuminating light beam 570 had it not been blocked by inner region 564 of apodizator 560 (FIG. 9A). The portion of bright-field light beam having the same geometrical location as illuminating light beam 570, is eventually blocked by bright-field filter 700 (FIG. 13B).

Thus, with reference to the system of FIG. 13C, the light which would eventually reach the bright-field detector, does not coincide with the illuminating light beam. This situation is similar to dark-field microscopes. In a dark-field microscope, the inspected surface is illuminated from significantly flat angles (i.e., almost parallel to the inspected surface), and the reflected light is detected at nearly right angles, above the inspected surface. The preceding situation is similar in that the angles at which the illuminating light hits the inspected surface and the angles at which detected light are reflected from the inspected surface, do not overlap.

In a further embodiment of the disclosed technique, continuous range magnification replaces the discrete values magnification which was provided by the interchangeable telescopes. A system according to this embodiment utilizes optical elements with zoom capabilities, to replace the multiple telescopes. Zoom capable optical element may include a teleconverter lens, a zoom capable telescope and the like. Such zoom capable optical elements allow adjustment of magnification level in a given range, without replacing the telescope. The present embodiment may include a single zoom capable optical element or a plurality of interchangeable zoom capable optical elements.

Figure 14:
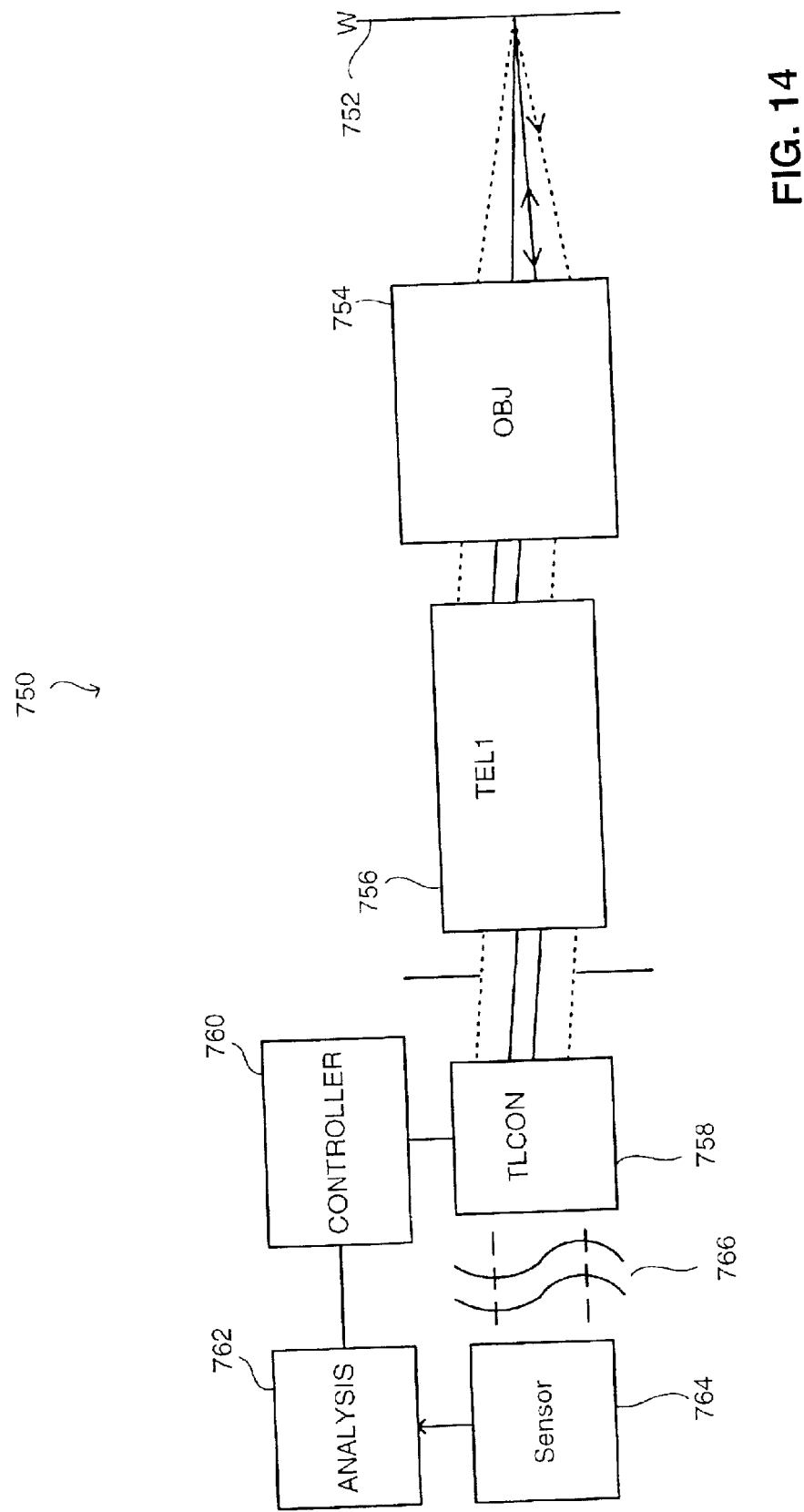
FIG. 14 is a schematic illustration of a system for scanning a wafer surface, according to another embodiment of the disclosed technique.

Reference is now made to FIG. 14, which is a schematic illustration of a system, generally referenced 750, for scanning a wafer surface, according to another embodiment of the disclosed technique. System 750 includes an automatic feedback magnification architecture for suspected defect analysis. In the present example, system 750 is used for scanning a wafer surface 752.

System 750 includes an objective lens assembly 754, a telescope 756, a controller 760, a teleconverter lens assembly 758 with zoom capabilities, an analysis module 762, a sensor 764 and an optical path (not detailed) 766.

Two elements are considered optically associated there between when they are positioned so as to allow light from one of the elements to enter the other element (e.g., by being placed along the same optical axis).

Telescope 756 is optically associated with objective lens assembly 754 and with teleconverter lens assembly 758. Teleconverter lens assembly 758 is further optically associated via optical path 766 (not detailed) to sensor 764. Analysis module 762 is coupled to sensor 764 and to controller 760. Controller 760 is further coupled to teleconverter lens assembly 758. System 750 may further include an illuminating light source (not shown).

System 750 is designed to allow a suspected defect detected on wafer 752 to be examined in increasingly greater levels of magnification, by using a continuous magnification level range. A continuous magnification range is achieved by optically associating teleconverter lens assembly 758 having zoom capabilities, with telescope 756. Teleconverter lens assembly 758 and telescope 756 both define a combined magnification range. Changing the optical setting of teleconverter lens assembly 758 effectively changes the focal length of telescope 756, thereby changing the combined magnification level, within the combined magnification range. Teleconverter lens assembly 758 further changes the angular width of illuminating light beams transmitted through teleconverter lens assembly 758 and telescope 756, thereby allowing control over scanning resolution of the inspected wafer surface.

Light from illuminating light source (not shown in Figure) is incident on wafer 752, either by oblique illumination, or by direct illumination via teleconverter lens assembly 758, telescope 756, and objective lens assembly 754. The angular width of the oblique illuminating light is set by optical elements in the oblique illuminating beam path (not shown in Figure). The angular width of direct illuminating beam can be modified by employing the zoom capabilities of teleconverter lens assembly 758.

Objective lens assembly 754 collects light reflected and scattered from wafer surface 752. Objective lens assembly 754 directs light to sensor 764 via telescope 756 and teleconverter lens assembly 758 and further via optical path 766 (not detailed in Figure). Sensor 764 detects light received from teleconverter lens assembly 758 and provides data respective of the detected light to analysis module 762. Analysis module 762 analyzes the received data and determines whether a suspected defect is classified as an actual defect, is classified as a detection error (no defect), or requires further analysis.

If the suspected defect is classified as an actual defect, analysis module 762 reports the detected defect and resumes scanning for further defects. If the suspected defect is determined to be a detection error, normal scanning is resumed. If the suspected defect is determined to require further analysis, then analysis module 762 determines the required magnification level, and provides a command to controller 760, to operate teleconverter lens assembly 758. Controller 760 operates teleconverter lens assembly 758 so as to adjust the magnification to the level determined by analysis module 762. System 750 then scans suspected defect area and repeats the process outlined using increasingly higher magnification levels, until suspected defect is classified.

Figure 15:
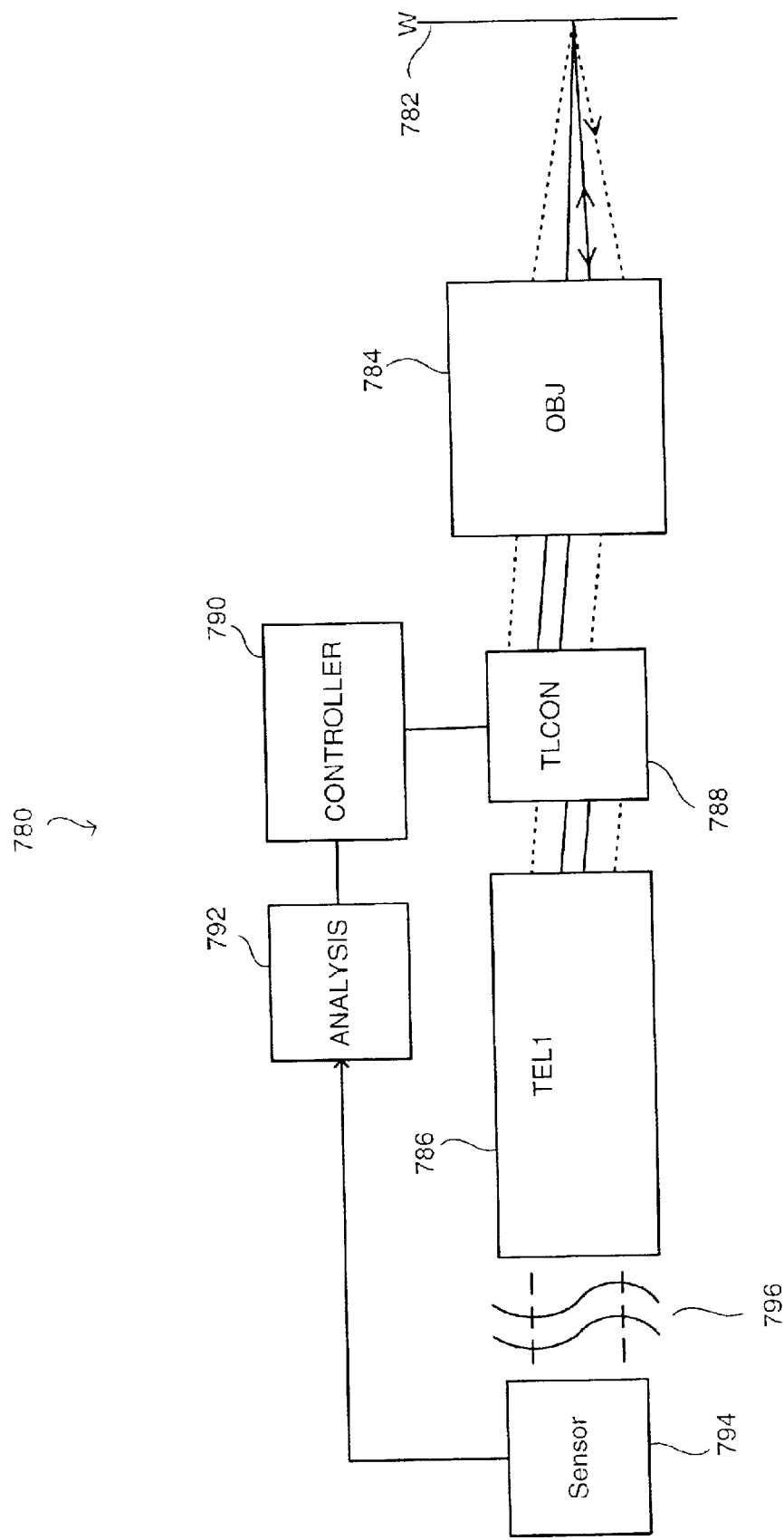
FIG. 15 is a schematic illustration of a system for scanning a wafer surface, according to a further embodiment of the disclosed technique.

Reference is now made to FIG. 15, which is a schematic illustration of a system, generally referenced 780, for scanning a wafer surface, according to a further embodiment of the disclosed technique. System 780 includes an automatic feedback magnification architecture for suspected defect analysis. In the present example, system 780 is used for scanning a wafer surface 782.

System 780 includes an objective lens assembly 784, a telescope 786, a teleconverter lens assembly 788 with zoom capabilities, a controller 790, an analysis module 792, a sensor 794 and an optical path (not detailed) 796.

Teleconverter lens assembly 788 is optically associated with objective lens assembly 784 and with telescope 786. Telescope 786 is further optically associated via optical path 796 (not detailed) to sensor 794. Analysis module 792 is coupled to sensor 794 and to controller 790, controller 790 is further coupled to teleconverter lens assembly 788. System 780 may further include an illuminating light source (not shown).

System 780 differs from system 750 (FIG. 14) in that the teleconverter lens is located between the telescope and the objective lens assembly (i.e., and not after the telescope and objective lens assembly).

Figure 16:
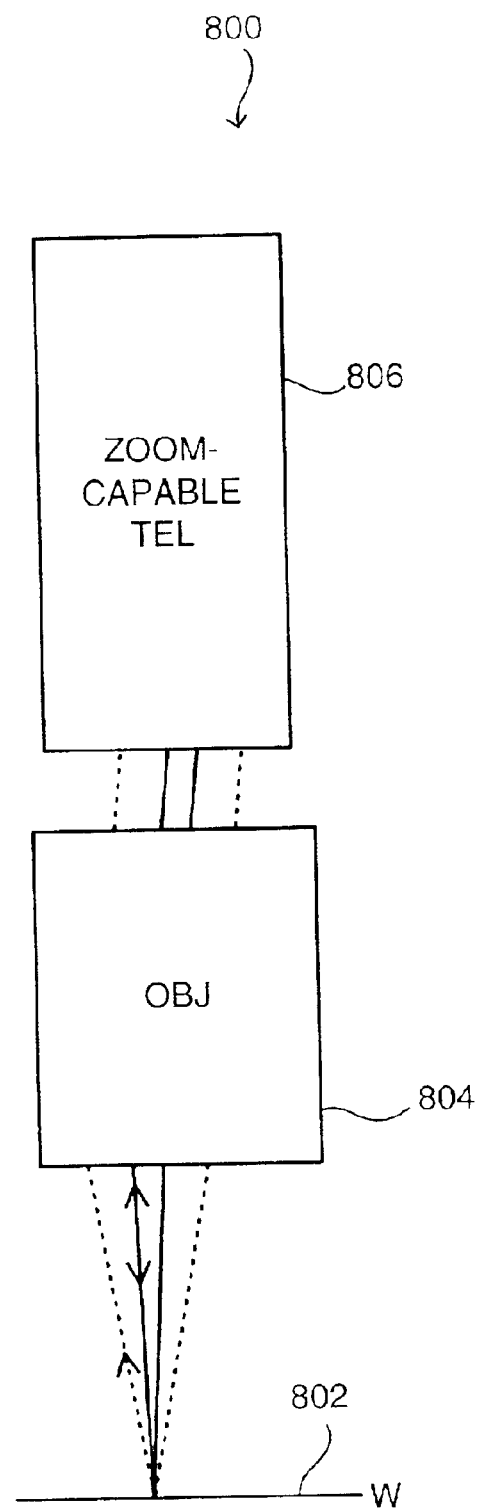
FIG. 16 is a schematic illustration of a front end optical assembly for scanning a wafer surface, according to another embodiment of the disclosed technique.

Reference is now made to FIG. 16, which is a schematic illustration of a front end optical assembly, generally referenced 800, for scanning a wafer surface, according to another embodiment of the disclosed technique. Front end optical assembly 800 may be incorporated in a scanning system with image analysis and automatic feedback for suspected defect analysis. In the present example, front end optical assembly 800 is used for scanning a wafer surface 802.

Front end optical assembly 800 includes an objective lens assembly 804 and a telescope 806 with zoom capabilities (also called zoom telescope). Telescope 806 may be further coupled to a controller (not shown), which controls the magnification thereof. Objective lens assembly 804 is optically associated with telescope 806. Telescope 806 is further optically associated via an optical path to a sensor (not shown). Front end optical assembly 800 is designed to allow a suspected defect detected on wafer 802 to be examined at increasingly greater levels of magnification, by using a continuous magnification range.

A continuous magnification range is achieved by utilizing a telescope 806, having zoom capabilities within a magnification range. Changing the zoom level setting for telescope 806, changes the magnification level, within the magnification range. Telescope 806 further changes the numerical aperture of the illuminating light beam, thereby allowing control over the scanning resolution of the inspected surface.

Light from an illuminating light source (not shown) is incident on wafer 802, either by oblique illumination, or by direct illumination via telescope 806 and objective lens assembly 804. The numerical aperture of oblique illuminating light is set by optical elements in oblique illuminating beam path (not shown). The numerical aperture of direct illuminating light beams can be modified by employing the zoom capabilities of telescope 806.

Front end optical assembly 800 differs from systems 750 and is 800, in that the zoom capable optical element is the telescope 806 (i.e., not a teleconverter lens). Other aspects of front end assembly 800 (e.g., automatic magnification change) are similar to those detailed for system 750.

Systems 750 and 780 (FIGS. 14 and 15), and front end assembly 800 (FIG. 16) reduce the need for replacing the telescope when magnification and scanning resolution changes are required, and further eliminate (or significantly reduce) the need for operator intervention.

Figure 17:
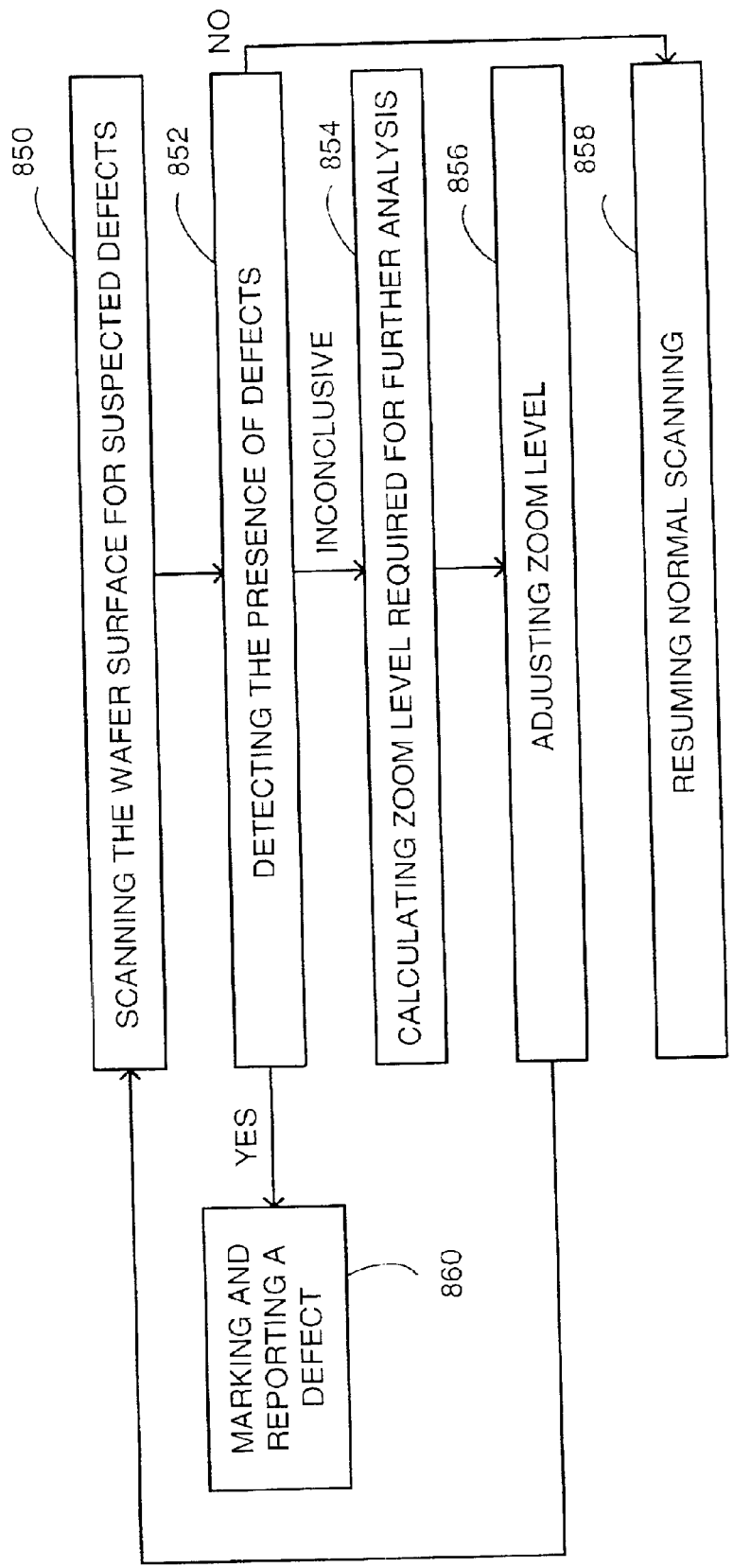
FIG. 17 is a schematic illustration of a method for operating either of the systems of FIGS. 14 and 15 or the front end assembly of FIG. 16, operative in accordance with another embodiment of the disclosed technique.

Reference is now made to FIG. 17, which is a schematic illustration of a method for operating either of systems 750, 780 and front end assembly 800 of FIGS. 14, 15 and 16, respectively, operative in accordance with another embodiment of the disclosed technique.

In procedure 850, the wafer surface is scanned for suspected defects, by detecting an image of a portion of the wafer surface. In the example set forth in FIG. 14, the wafer surface 752 is scanned by illuminating light beams, and collected light is transmitted to sensor 764 via the optical path.

In procedure 852, the presence of defects is detected, by analyzing the detected image. In the example set forth in FIG. 14, analysis module 762 analyzes data provided from sensor 764, to determine areas of suspected defects.

If the presence of defects is not detected, then the system resumes normal processing (procedure 858). Otherwise, if the presence of a defect is detected, then this defect is marked and reported (procedure 860). Finally, if the detection of the presence of defects is inconclusive, then the system proceeds to procedure 854.

In procedure 854, a zoom level which is required for further analysis, is calculated. In the example set forth in FIG. 14, analysis module 762, calculates a zoom level which is required for further analysis.

In procedure 856, the zoom level is adjusted to the level calculated in procedure 854. In the example set forth in FIG. 14, analysis module 762 provides a command to controller 760 to operate teleconverter lens assembly 758. Controller 760 then operates teleconverter lens assembly 758 to change the magnification level to that calculated by analysis module 762. After the zoom level is adjusted in procedure 856, the system proceeds to procedure 850 to perform further analysis of suspected defect areas. In the example set forth in FIG. 14, the suspected area is scanned again using a higher magnification level. The process illustrated is repeated until the suspected defect is classified as an actual defect or a false detection.

According to another aspect of the disclosed technique, there is provided a novel structure of the gray-field detector. The novel gray-field detector is divided into a plurality of zones. Each zone is detected independently, and thus, the combined results provide supplementary information about the inspected wafer surface.

Figure 18:
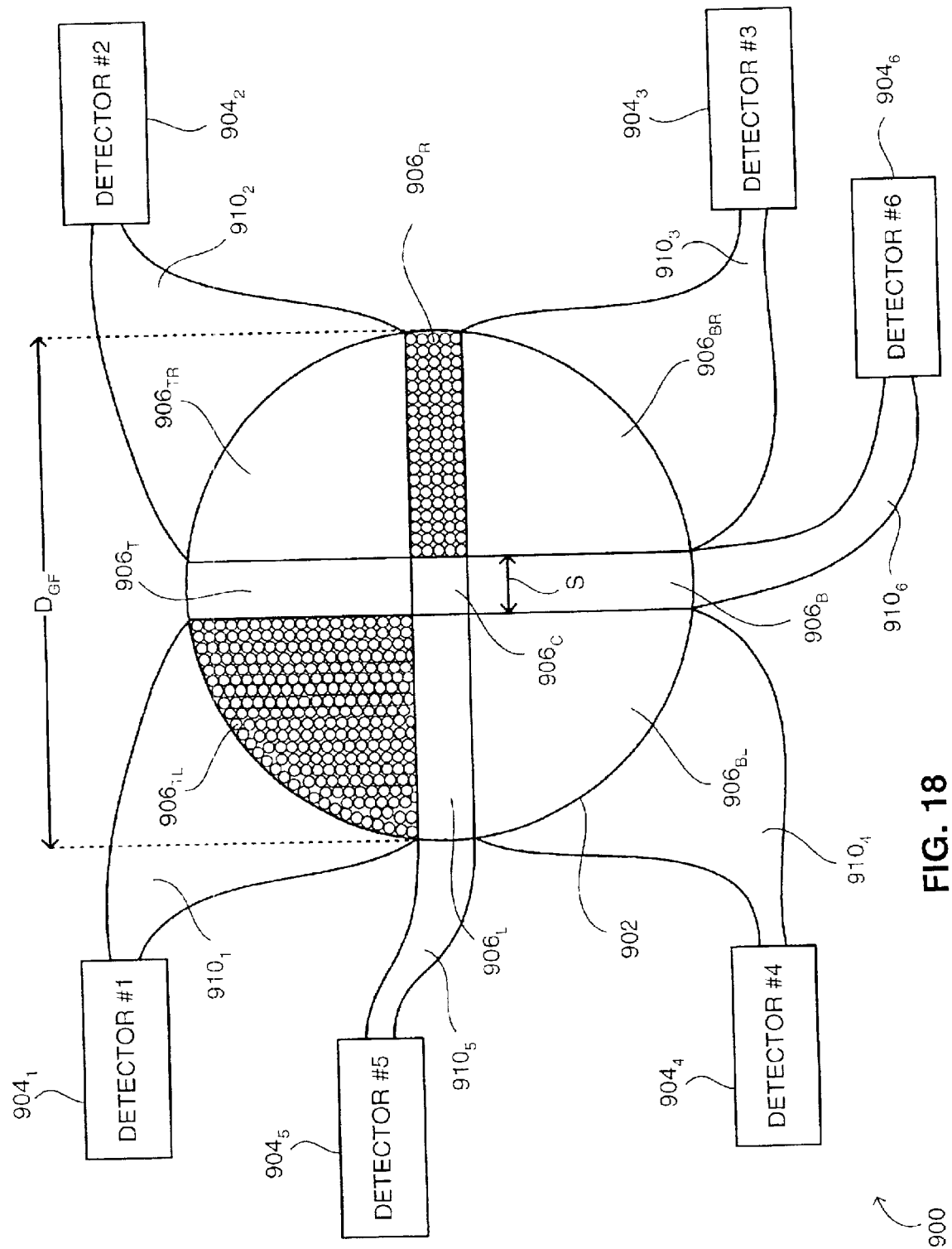
FIG. 18 is a schematic illustration of a multi-zone gray-field detector constructed and operative in accordance with a further embodiment of the disclosed technique.

Reference is now made to FIG. 18, which is a schematic illustration of a multi-zone gray-field detector, generally referenced 900, constructed and operative in accordance with a further embodiment of the disclosed technique. Multi-zone gray-field detector 900 includes a gray-field collector 902, light guides 910$_1$, 910$_2$, 910$_3$, 910$_4$, 910$_5$ and 910$_6$, and light detectors 904$_1$, 904$_2$, 904$_3$, 904$_4$, 904$_5$ and 904$_6$.

Gray-field pupil collector 902 is circular at a diameter $D_{GF}$. Gray-field collector 902 is located at a pupil of the scanning system. It is noted that diameter $D_{GF}$ may be set at any size, depending on the size of the image, which is produced at the pupil of gray-field collector 902. Gray-field collector 902 includes a right section 906$_R$, a left section 906$_L$, a top section 906$_T$, a bottom section 906$_B$, a top-right section 906$_{TR}$, a bottom-right section 906$_{BR}$, a top-left section 906$_{TL}$, a bottom-left section 906$_{BL}$ and a central section 906$_C$. Central section 906$_C$ is positioned at the center of light collector $D_{GF}$. Central section 906$_C$ is a square of side S.

Right section 906$_R$ is a horizontal strip of width S. The left boundary of right section 906$_R$ is a straight line coinciding with the right boundary of central section 906$_C$. The top boundary of right section 906$_R$ is a straight line extending the top boundary of central section 906$_C$. The bottom boundary of right section 906$_R$ is a straight line extending the bottom boundary of central section 906$_C$. The right boundary of right section 906$_R$ is an arc coinciding with a portion of the boundary of gray-field collector 902. Left section 906$_L$ and right section 906$_R$ are symmetrical with respect to the vertical diameter of gray-field collector 902. Top section 906$_T$ and bottom section 906$_B$ are identical to right section 906$_R$ and left section 906$_L$, but rotated by 90 degrees there from. Top-right section 906$_{TR}$ has a left boundary coinciding with the right boundary of top section 906$_T$, a bottom boundary coinciding with the top boundary of right section 906$_R$, and a top-right boundary coinciding with a portion of the boundary of gray-field collector 902. Similarly, bottom-right section 906$_{BR}$, top-left section 906$_{TL}$ and bottom-left section 906$_{BL}$ complete the circular region occupied by gray-field collector 902.

Each section of gray-field collector 902, except for central section 906$_C$, is optically coupled to a respective light detector in a manner that the light incident upon that section, is directed to that respective light detector. It is noted that more than one section can be optically coupled to the same light detector. Different light guiding elements can be used for optically coupling the sections to their respective light detectors, such as optic fiber, specific shape molded transparent light guides, mirrors, and the like. In the example set forth in FIG. 18, each of light guides 910$_1$, 910$_2$, 910$_3$, 910$_4$, 910$_5$ and 910$_6$, includes a plurality of optical fibers.

Light guide 910$_1$ optically couples top-left section 906$_{TL}$ to light detector 904$_1$. Light guide 910$_2$ optically couples top-right section 906$_{TR}$ to light detector 904$_2$. Light guide 910$_3$ optically couples left section 906$_L$ and right section 906$_R$ to light detector 904$_3$. Light guide 910$_4$ optically couples bottom-left section 906$_{BL}$ to light detector 904$_4$. Light guide 910$_5$ optically couples left section 906$_L$ and right section 906$_R$ to light detector 904$_5$. Light guide 910$_6$ optically couples bottom section 906$_L$ and top section 906$_T$ to light detector 904$_6$.

It is noted that gray-field detector 900 may include additional optical elements, such as a relay lens assembly, which is located in front of the gray-field pupil. Such a relay lens assembly, produces the gray-field portion of the image of a pupil of the scanning system, at gray-field collector 902.

It is further noted that, unlike conventional gray-field detectors which provide information respective of the amount of gray-field light, light detectors 904$_1$, 904$_2$, 904$_3$, 904$_4$, 904$_5$ and 904$_6$ provide information respective of angular and spatial distribution of the gray-field light. The information provided by light detectors 904$_1$, 904$_2$, 904$_3$, 904$_4$, 904$_5$ and 904$_6$, significantly increases the amount and quality of inspection information, and hence ability to detect defects in the scanned surface.

Figure 19:
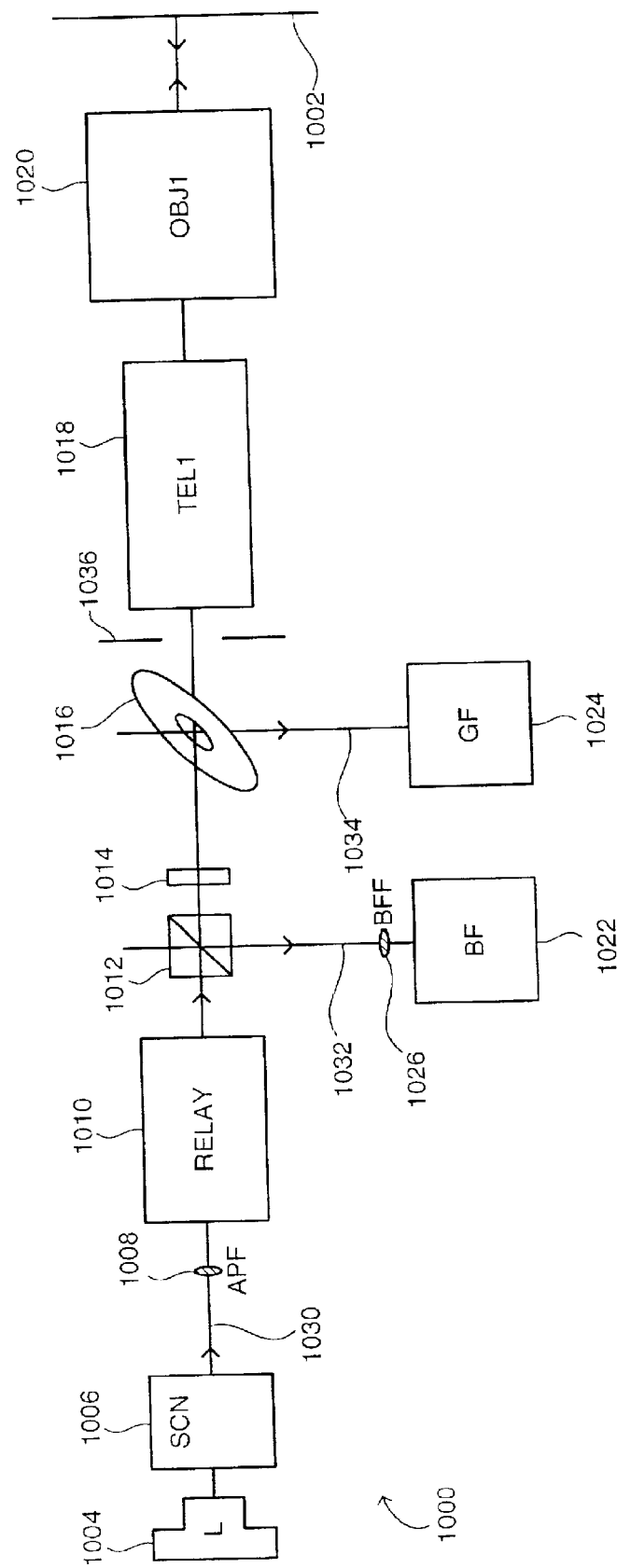
FIG. 19 is a schematic illustration of a system for scanning a wafer surface, constructed and operative in accordance with another embodiment of the disclosed technique.

Several aspects of the disclosed technique, which are illustrated in the drawings discussed hereinabove, may be combined in a single system. Reference is now made to FIG. 19, which is a schematic illustration of a system, generally referenced 1000, for scanning a wafer surface, constructed and operative in accordance with another embodiment of the disclosed technique. In the example set forth in FIG. 19, system 1000 is used for scanning a surface 1002. It is noted that system 1000 is not drawn to scale. System 1000 includes a laser light source 1004, a scanner 1006, an apodizator 1008, a relay lens assembly 1010, a polarizing beam splitter 1012, a quarter wave plate 1014, an annular mirror 1016, an aperture stop 1036, a telescope 1018, an objective lens assembly 1020, a bright-field filter 1026, a bright-field detector 1022 and a gray-field detector 1024.

Laser light source 1004, scanner 1006, aperture stop 1036, telescope 1018 and objective lens 1020 are generally similar to laser light source 204, scanner 206, aperture stop 218, telescope 216 and objective lens assembly 222 (FIG. 3), respectively. Objective lens assembly 1020 has a high numerical aperture. System 1000 includes additional telescopes (not shown) which are interchangeable with telescope 1020.

Polarizing beam splitter 1012, quarter wave plate 1014, annular mirror 1016 and bright-field detector 1022 are generally similar to polarizing beam splitter 366, quarter wave plate 368, annular mirror 370 and bright-field detector 378 (FIG. 5), respectively. Gray-field detector 1024 is generally similar to multi-zone gray-field detector 900 (FIG. 18).

Apodizator 1008 and relay lens assembly 1010 are generally similar to apodizator 428 and relay lens assembly 440 (FIG. 6), respectively. Bright-field filter 1026 is generally similar to bright-field filter 700 (FIG. 13B). System 1000 may further include additional apodizators (not shown) which are interchangeable with apodizator 1008.

Laser light source 1004, scanner 1006, apodizator 1008, relay lens assembly 1010, polarizing beam splitter 1012, quarter wave plate 1014, annular mirror 1016, telescope 1018, objective lens assembly 1020 and wafer surface 1012 are positioned along a first optical axis 1030. First optical axis 1030 is perpendicular to surface 1002.

Scanner 1006 is positioned between laser light source 1004 and apodizator 1008. Relay lens assembly 1010 is positioned between apodizator 1008 and polarizing beam splitter 1012. Quarter wave plate 1014 is positioned between polarizing beam splitter 1012 and annular mirror 1016. Aperture stop 1036 is positioned between annular mirror 1016 and telescope 1018. Objective lens assembly 1020 is positioned between telescope 1018 and surface 1002.

Polarizing beam splitter 1012, bright-field filter 1026 and bright-field detector 1022 are positioned along a second optical axis 1032. Bright-field filter 1026 is positioned between polarizing beam splitter 1012 and bright-field detector 1022. In the present example, second optical axis 1032 is perpendicular to first optical axis 1030.

Annular mirror 1016 and gray-field detector 1024 are positioned along a third optical axis 1034. In the present example, third optical axis 1034 is parallel to second optical axis 1032. It is noted that the arrows on optical axes 1030, 1032 and 1034, merely indicate the general directions of light beam progression there along and not the light beams themselves, which are not shown. Polarizing beam splitter 1012 includes a semi-transparent reflection plane 1026. In the present example, semi-transparent reflection plane 1026 is oriented at 45 degrees relative to optical axes 1030 and 1032. Annular mirror 1016 is also oriented at 45 degrees relative to optical axes 1030 and 1032.

Laser 1004 emits a laser light beam (not shown) toward scanner 1006. Scanner 1006 receives the laser light beam and produces an illuminating light beam (not shown). The illuminating beam passes successively through scanner 1006, apodizator 1008, relay lens assembly 1010, polarizing beam splitter 1012, quarter wave plate 1014, annular mirror 1016, aperture stop 1036, telescope 1018, and finally objective lens assembly 1020. The illuminating light beam then reaches surface 1002. Surface 1002 reflects the illuminating light beam, thereby producing a bright-field light beam and a gray-field light beam (both not shown). The combined bright-field and gray-field light beam passes through objective lens assembly 1020, aperture stop 1036 and telescope 1018. Annular mirror 1016 reflects the gray-field light beam toward gray-field detector 1024, which detects the intensity thereof. The bright-field light beam passes through the aperture of annular mirror 1016, and further through quarter wave plate 1014. Semi-transparent reflection plane 1026 reflects the bright-field light beam towards bright-field detector 1022, which detects the intensity thereof.

It is noted that the combination of the single, high numerical aperture objective lens assembly 1020, the annular mirror 1016 and the polarizing beam splitter 1012, significantly increases the gray-field numerical aperture at an efficient cost, thereby significantly increasing the amount of data which is accumulated in the scanning process. This is due to the fact that the novel optical structure of the annular mirror 1016 and polarizing beam splitter 1012, does not limit the numerical aperture of the gray-field light beam which is transferred thereby toward the gray-field detector. As a result, the maximal numerical aperture of this gray-field image mostly depends on the numerical aperture of the objective lens assembly 1020.

It is further noted that the combination of apodizator 1008 and bright-field filters 1026, enables a mode of operation similar to that of a dark-field microscope, in that the illuminating light is incident on the wafer surface at angles which are not detected by the bright-field detector. Combined with telescope 1018, the combination of apodizator 1008 and bright-field filters 1026, further enhances the similarity to microscope dark-field mode. It is noted that some telescopes are designed so as to increase the numerical aperture of the illuminating light beam and the bright-field light beam. Thus, the illuminating light and the detected light still do not intersect, but the surface is illuminated from angles which are further flattened, closer to the angles of illumination in dark-field microscopes.

It is still further noted that system 1000 is characterized by a high gray-field numerical aperture, which significantly increases the information which is embedded in the gray-field light beam. This information is detected at great detail by gray-field detector 1024.

Figure 20:
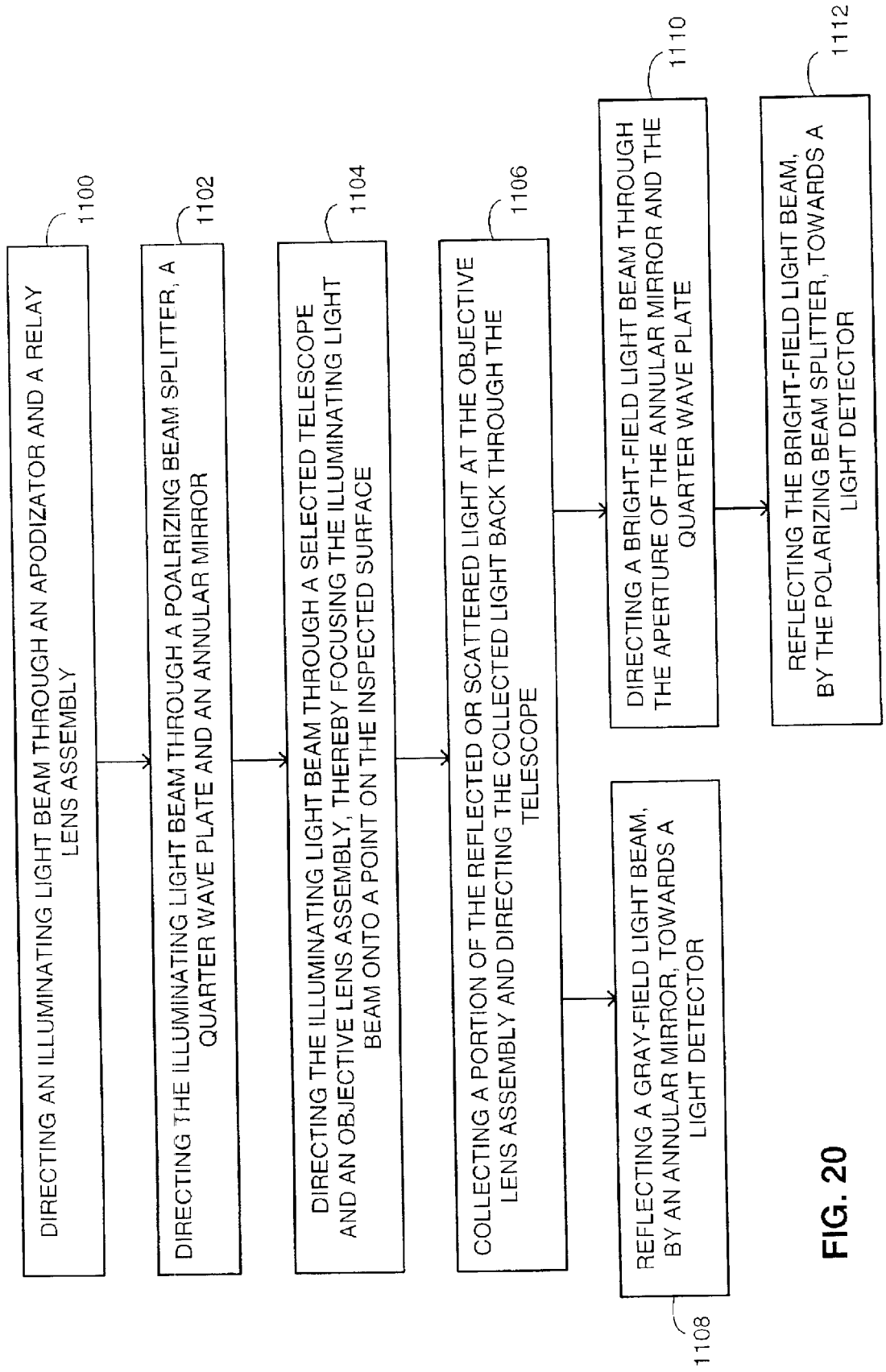
FIG. 20 is a schematic illustration of a method for inspecting a surface, in accordance with another embodiment of the disclosed technique.

Reference is now made to FIG. 20, which is a schematic illustration of a method for inspecting a surface, in accordance with another embodiment of the disclosed technique. In procedure 1100, an illuminating light beam is directed through an apodizator and a relay lens assembly. In the example set forth in FIG. 19, laser 1004 and scanner 1006 produce the illuminating light beam (not shown), which is directed through apodizator 1008 and relay lens assembly 1010.

In procedure 1102, the illuminating light beam is directed through a polarizing beam splitter, a quarter wave plate and an annular mirror. In the example set forth in FIG. 1004, the illuminating light beam is directed through polarizing beam splitter 1012 and quarter wave plate 1014.

In procedure 1104, the illuminating light beam is directed through a selected telescope and an objective lens assembly, thereby focusing the illuminating light beam onto a point on the inspected surface. In the example set forth in FIG. 19, the illuminating light beam is directed through telescope 1018 and objective lens assembly 1020, whereby the illuminating light beam is focused onto a point on inspected surface 1002.

In procedure 1106, a portion of the reflected or scattered light is collected at the objective lens assembly, and the collected light is directed back through the telescope. In the example set forth in FIG. 19, the illuminating light beam reflected and scattered from surface 1002, and a portion of the scattered and reflected light is directed back through objective lens assembly 1020 and telescope 1018.

In procedure 1108, gray-field light beam is reflected by an annular mirror, towards a light detector. In the example set forth in FIG. 19, annular mirror 1016 reflects the gray-field light beam towards gray-field detector 1024.

In procedure 1110, a bright-field light beam is directed through the aperture of the annular mirror and the quarter wave plate. In the example set forth in FIG. 19, the bright-field light beam passes through the aperture of annular mirror 1016, and further through quarter wave plate 1014.

In procedure 1112, the bright-field light beam is reflected, at the polarizing beam, towards a light detector. In the example set forth in FIG. 19, semi-transparent reflection plane 1026 reflects the bright-field light beam towards bright-field detector 1022. It is noted that procedures 1108 and 1110 are performed independently and may be generally executed in any order or concurrently.

It will be appreciated by persons skilled in the art that the disclosed technique is not limited to what has been particularly shown and described hereinabove. Rather the scope of the disclosed technique is defined only by the claims, which follow.

What is claimed is:

1. System for scanning a surface, comprising:
    a light source producing an illuminating light beam;
    an objective lens assembly, located between said light source and said surface;
    at least one light detector;
    an apodizator located between said light source and said objective lens assembly;
    a relay lens assembly located between said apodizator and said objective lens assembly; and
    a polarizing beam splitter located between said relay lens assembly and said objective lens assembly.

2. The system according to claim 1, wherein said light source produces an image of said illuminating light beam on said apodizator,
    wherein said apodizator blocks at least a portion of said illuminating light beam,
    and wherein said relay lens assembly images said blocked illuminating light beam at an entrance pupil of said objective lens assembly.

3. The system of claim 1 wherein said illuminating light beam travels through said polarizing beam splitter, and said objective lens assembly toward said surface, which in turn reflects said reflected light beam,
    wherein at least a portion of said reflected light beam travels through said objective lens assembly,
    wherein said polarizing beam splitter deflects at least a portion of said at least portion of said reflected light beam, toward at least one of said at least one light detector.

4. The system of claim 1 further comprising an annular mirror located between said polarizing beam splitter and said at least one of said at least one light detector,
    wherein said annular mirror admits the bright-field portion of said at least a portion of said reflected light beam through an aperture therein, and wherein said annular mirror reflects the gray-field portion of said at least a portion of said reflected light beam toward at least another of said at least one light detector.

5. The system of claim 4 further comprising another relay lens assembly, located between said polarizing beam splitter and said annular mirror, producing an image of said surface, on said aperture.

6. The system of claim 1, wherein said light source produces said illuminating light beam, so as to scan said surface.

7. The system of claim 1, wherein said surface is selected from the light consisting of:
    a wafer;
    a mask;
    printed material; and
    fabric.

8. The system of claim 1, further comprising a quarter wave plate located between said polarizing beam splitter and said objective lens assembly,
    wherein said illuminating light beam is linearly polarized before passing through said quarter wave plate.

9. The system of claim 1, further comprising a plurality of interchangeable telescopes, a selected one of said interchangeable telescopes being located between said relay lens assembly and said objective lens assembly, adjacent to said objective lens assembly.

10. The system of claim 9, further comprising an interchanging mechanism,
    wherein at least selected ones of said interchangeable telescopes are located on said interchanging mechanism, interchanging to a selected telescope when one is selected.

11. The system of claim 10, wherein said interchanging mechanism is selected from the list consisting of:
    a turret; and
    a slide.

12. The system of claim 9, further comprising an analysis module, coupled to said at least one light detector.

13. The system of claim 9, further comprising a teleconverter lens assembly, optically associated with said selected one of said interchangeable telescopes.

14. The system of claim 13, wherein said teleconverter lens assembly is located between said selected one of said interchangeable telescopes and said objective lens assembly.

15. The system of claim 13, wherein said selected one of said interchangeable telescopes is located between said teleconverter lens assembly and said objective lens assembly.

16. The system of claim 13, further comprising a controller coupled said teleconverter lens assembly, wherein said controller operates said teleconverter lens assembly to adjust the combined magnification of said teleconverter lens assembly and said selected one of said interchangeable telescopes.

17. The system of claim 16, further comprising an analysis module, coupled to said at least one light detector and to said controller,
    wherein said analysis module analyzes light readings provided from said at least one light detector, for the purpose of detecting defects, said analysis module determining a new magnification level when detecting a suspected defect, and instructing said controller to operate said teleconverter lens assembly to adjust to said combined magnification to said new magnification level.

18. The system of claim 9, wherein at least one of said interchangeable telescopes comprises a zoom telescope.

19. The system of claim 18, further comprising a controller coupled to said zoom telescope, wherein said controller operates said zoom telescope to adjust the magnification of said zoom telescope.

20. The system of claim 19, further comprising an analysis module, coupled to said at least one light detector and to said controller,
wherein said analysis module analyzes light readings provided from said at least one light detector, for the purpose of detecting defects, said analysis module determining a new magnification level when detecting a suspected defect, and instructing said controller to operate said zoom telescope to adjust to said magnification to said new magnification level.

21. The system of claim 9, wherein said objective lens assembly is located at a fixed distance from said surface, for each selection of said interchangeable telescope.

22. The system of claim 1, further comprising an annular mirror located between said relay lens assembly and said objective lens assembly, said annular mirror admitting said illuminating light beam and deflecting at least a portion of a reflected light beam received from said objective lens assembly toward at least one of said at least one light detector.

23. The system according to claim 22, further comprising a polarizing beam splitter, located between said relay lens assembly and said annular mirror, admitting said illuminating light beam and deflecting at least a portion of said reflected light beam admitted through said annular mirror toward at least another of said at least one light detector.

24. The system according to claim 22, wherein said at least one of at least one light detector is a gray-field light detector.

25. The system according to claim 24, wherein said at least other of said at least one light detector is a bright-field light detector.

26. The system of claim 23, further comprising a quarter wave plate located between said polarizing beam splitter and said annular mirror,
wherein said illuminating light beam is linearly polarized before passing through said quarter wave plate.

27. The system of claim 22, wherein said at least portion of said reflected light beam, reflected by said annular mirror, is defined as a gray-field reflected light beam.

28. The system of claim 22, wherein light reflected by said annular mirror, is defined as a gray-field reflected light beam.

29. The system of claim 23, wherein light reflected by said polarizing beam-splitter, is defined as a bright-field reflected light beam.

30. The system of claim 22, wherein the inner diameter of said annular mirror is in the order of the diameter of said illuminating light beam, immediately prior to passing through said annular mirror.

31. The system of claim 23, wherein the deflecting plane of said polarizing beam splitter is limited to the order of the width of said at least a portion of said reflected light beam admitted through said annular mirror, right before being deflected by said polarizing beam splitter.

32. The system of claim 22, further comprising an additional relay lens assembly located between said annular mirror and said objective lens assembly.

33. The system according to claim 1, wherein said apodizator is interchangeable, and wherein said system further comprises additional interchangeable apodizators.

34. The system according to claim 1, wherein said apodizator is dynamic, operative to block different portions of said illuminating light beams.

35. System for scanning a surface, comprising:
a light source producing an illuminating light beam;
an objective lens assembly, located between said light source and said surface;
at least one light detector;
an apodizator located between said light source and said objective lens assembly;
a relay lens assembly located between said apodizator and said objective lens assembly; and
an annular mirror located between said relay lens assembly and said objective lens assembly, said annular mirror admitting said illuminating light beam and deflecting at least a portion of a reflected light beam received from said objective lens assembly toward at least one of said at least one light detector.

36. The system according to claim 35, further comprising a polarizing beam splitter, located between said relay lens assembly and said annular mirror, admitting said illuminating light beam and deflecting at least a portion of said reflected light beam admitted through said annular mirror toward at least another of said at least one light detector.

37. The system according to claim 35, wherein said at least one of said at beast one light detector is a gray-field light detector.

38. The system according to claim 37, wherein said at least other of said at least one light detector is a bright-field light detector.

39. The system of claim 36, further comprising a quarter wave plate located between said polarizing beam splitter and said annular mirror,
wherein said illuminating light beam is linearly polarized before passing through said quarter wave plate.

40. The system of claim 35, wherein said at least portion of said reflected light beam, reflected by said annular mirror, is defined as a gray-field reflected light beam.

41. The system of claim 35, wherein light reflected by said annular mirror, is defined as a gray-field reflected light beam.

42. The system of claim 36, wherein light reflected by said polarizing beam-splitter, is defined as a bright-field reflected light beam.

43. The system of claim 35, wherein the inner diameter of said annular mirror is in the order of the diameter of said illuminating light beam, immediately prior to passing through said annular mirror.

44. The system of claim 36, wherein the deflecting plane of said polarizing beam splitter is limited to the order of the width of said at least a portion of said reflected light beam admitted through said annular mirror, right before being deflected by said polarizing beam splitter.

45. The system of claim 35, further comprising an additional relay lens assembly located between said annular mirror and said objective lens assembly.

* * * * *